US011331797B2

(12) United States Patent
Takagi

(10) Patent No.: US 11,331,797 B2
(45) Date of Patent: May 17, 2022

(54) CONTINUUM ROBOT, MODIFICATION METHOD OF KINEMATIC MODEL OF CONTINUUM ROBOT, AND CONTROL METHOD OF CONTINUUM ROBOT

(71) Applicant: CANON KABUSHIKI KAISHA, Tokyo (JP)

(72) Inventor: Kiyoshi Takagi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 450 days.

(21) Appl. No.: 16/317,498

(22) PCT Filed: Jul. 5, 2017

(86) PCT No.: PCT/JP2017/024599
§ 371 (c)(1),
(2) Date: Jan. 11, 2019

(87) PCT Pub. No.: WO2018/012360
PCT Pub. Date: Jan. 18, 2018

(65) Prior Publication Data
US 2019/0321976 A1 Oct. 24, 2019

(30) Foreign Application Priority Data

Jul. 13, 2016 (JP) .............................. JP2016-138133

(51) Int. Cl.
*B25J 9/16* (2006.01)
*B25J 18/06* (2006.01)
*A61M 25/01* (2006.01)

(52) U.S. Cl.
CPC ............. *B25J 9/1625* (2013.01); *B25J 18/06* (2013.01); *A61M 25/0116* (2013.01)

(58) Field of Classification Search
CPC .... B25J 9/1625; B25J 18/06; A61M 25/0116; A61B 2034/301; A61B 34/71; A61B 34/30; G05B 2219/40234
See application file for complete search history.

(56) References Cited

U.S. PATENT DOCUMENTS

| 8,671,817 | B1 * | 3/2014 | Bogusky | ................. D04C 3/48 87/35 |
| 9,011,318 | B2 * | 4/2015 | Choset | ................... A61B 34/30 600/114 |

(Continued)

FOREIGN PATENT DOCUMENTS

| CN | 102596062 A | 7/2012 |
| CN | 105729458 A | 7/2016 |

(Continued)

OTHER PUBLICATIONS

Neumann, M., et al., "Considerations for Follow-the-Leader Motion of Extensible Tendon-drive Continuum Robots", IEEE International Conference on Robotics and Automation, May 16-21, 2016, pp. 917-923.

(Continued)

*Primary Examiner* — Bhavesh V Amin
(74) *Attorney, Agent, or Firm* — Canon U.S.A., Inc., IP Division

(57) ABSTRACT

A continuum robot includes a curvable first curvable portion, a curvable second curvable portion provided adjacent to the first curvable portion, a first wire connected to the first curvable portion, a second wire connected to the second curvable portion, and a control unit which controls curves of the first curvable portion and the second curvable portion by controlling driving of the first wire and the second wire. The control unit controls driving of the first wire and the second wire on the basis of a kinematic model in consideration of a curve of the second curvable portion accompanying driv- (Continued)

ing the first wire and a curve of the first curvable portion accompanying driving of the second wire. Alternatively, the control unit controls driving of the first wire and the second wire so that a curve target value of the first curvable portion is achieved by the sum of curved amounts of the first curvable portion and the second curvable portion.

16 Claims, 31 Drawing Sheets

(56) References Cited

U.S. PATENT DOCUMENTS

| | | | | |
|---|---|---|---|---|
| 9,591,964 B2* | 3/2017 | Choset | ............... | A61B 1/0016 |
| 9,808,140 B2* | 11/2017 | Belson | ............... | A61B 1/05 |
| 9,901,410 B2* | 2/2018 | Oyola | ............... | A61B 34/30 |
| 10,076,235 B2* | 9/2018 | Choset | ............... | A61B 34/70 |
| 10,149,607 B2* | 12/2018 | Choset | ............... | A61B 1/31 |
| 10,543,605 B2* | 1/2020 | Piette | ............... | B25J 9/0018 |
| 10,743,750 B2* | 8/2020 | Hunter | ............... | A61B 1/0057 |
| 2003/0120183 A1* | 6/2003 | Simmons | ............... | G06F 3/011 |
| | | | | 600/595 |
| 2007/0161861 A1* | 7/2007 | Kawai | ............... | A61B 1/0016 |
| | | | | 600/145 |
| 2007/0208458 A1* | 9/2007 | Harada | ............... | B25J 17/0283 |
| | | | | 700/245 |
| 2008/0287963 A1* | 11/2008 | Rogers | ............... | A61B 34/71 |
| | | | | 606/130 |
| 2009/0171151 A1* | 7/2009 | Choset | ............... | A61B 1/31 |
| | | | | 600/114 |
| 2010/0010504 A1* | 1/2010 | Simaan | ............... | A61B 34/76 |
| | | | | 606/130 |
| 2011/0241368 A1* | 10/2011 | Kurita | ............... | B25J 15/0009 |
| | | | | 294/213 |
| 2011/0312841 A1* | 12/2011 | Silverbrook | ...... | B01L 3/502707 |
| | | | | 506/40 |
| 2013/0269466 A1 | 10/2013 | Zubiate | | |
| 2013/0300537 A1 | 11/2013 | Bajo | | |
| 2014/0148673 A1* | 5/2014 | Bogusky | ............... | A61M 25/0012 |
| | | | | 600/374 |
| 2014/0148759 A1* | 5/2014 | Macnamara | ...... | A61M 25/0147 |
| | | | | 604/95.04 |
| 2014/0309625 A1* | 10/2014 | Okamoto | ............... | A61B 34/71 |
| | | | | 606/1 |
| 2014/0330432 A1* | 11/2014 | Simaan | ............... | A61B 34/35 |
| | | | | 700/250 |
| 2015/0088161 A1 | 3/2015 | Hata | | |
| 2015/0164491 A1* | 6/2015 | Choset | ............... | A61B 34/70 |
| | | | | 600/417 |
| 2015/0343647 A1* | 12/2015 | Garcia | ............... | B25J 15/083 |
| | | | | 294/200 |
| 2016/0164384 A1* | 6/2016 | Johnson | ............... | F16C 19/10 |
| | | | | 310/85 |
| 2016/0174816 A1* | 6/2016 | Choset | ............... | A61B 34/20 |
| | | | | 600/142 |
| 2017/0014998 A1* | 1/2017 | Langenfeld | ............... | B25J 9/161 |
| 2017/0049298 A1* | 2/2017 | Hunter | ............... | A61B 1/00105 |
| 2017/0156569 A1* | 6/2017 | Choset | ............. | A61B 17/00234 |
| 2018/0099422 A1* | 4/2018 | Yoon | ............... | B25J 13/084 |
| 2018/0207803 A1* | 7/2018 | Takase | ............... | B25J 18/02 |
| 2018/0209822 A1* | 7/2018 | Kondo | ............... | B25J 13/089 |
| 2018/0296282 A1* | 10/2018 | Kose | ............... | A61B 1/0053 |
| 2018/0304458 A1* | 10/2018 | Takagi | ............... | B25J 18/06 |
| 2019/0184553 A1* | 6/2019 | Takagi | ............... | B25J 9/1625 |
| 2019/0274521 A1* | 9/2019 | Choset | ............. | A61B 1/00006 |
| 2019/0321976 A1* | 10/2019 | Takagi | ............... | B25J 9/1625 |
| 2020/0375682 A1* | 12/2020 | Kincaid | ............... | A61B 34/76 |

FOREIGN PATENT DOCUMENTS

| | | |
|---|---|---|
| JP | 2007292276 A | 11/2007 |
| JP | 4781492 B2 | 9/2011 |

OTHER PUBLICATIONS

Webster III, R. J., et al., "Design and Kinematic Modeling of Constant Curvature Continuum Robots: A Review", The International Journal of Robotics Research, Nov. 2010, pp. 1661-1683, vol. 29, No. 13.

* cited by examiner

[Fig. 1]
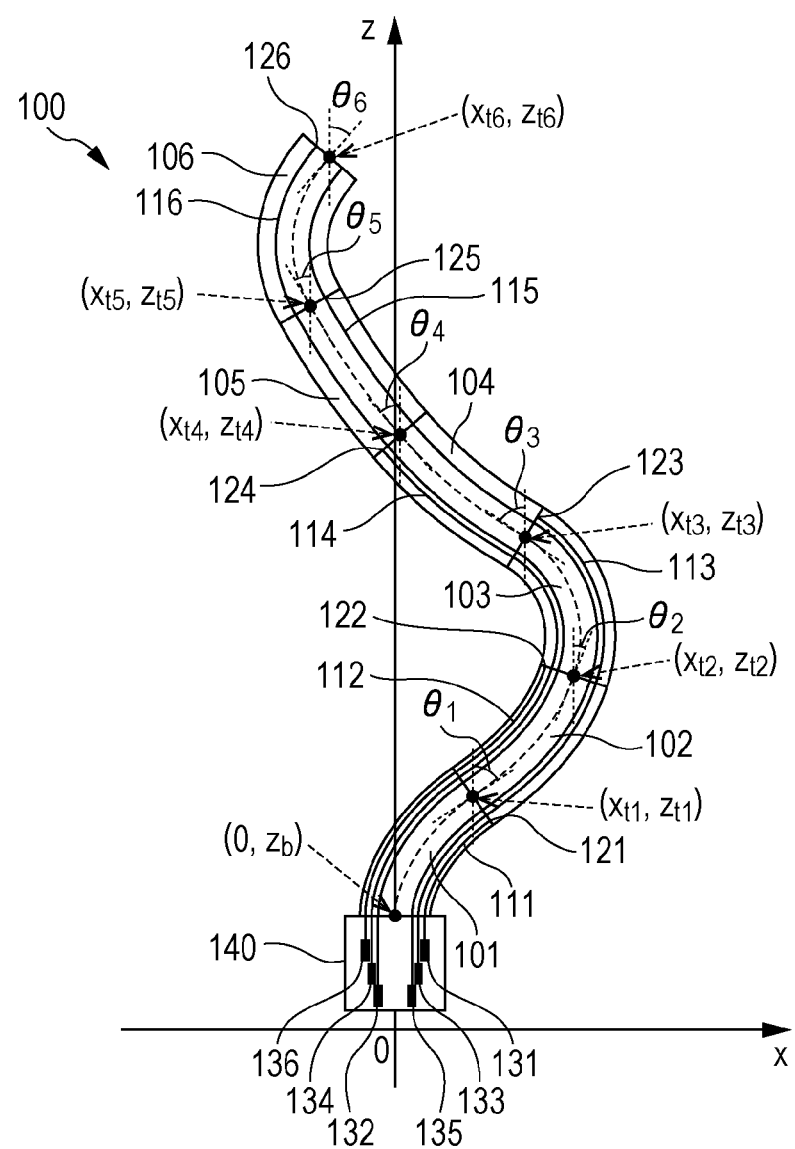

[Fig. 2]
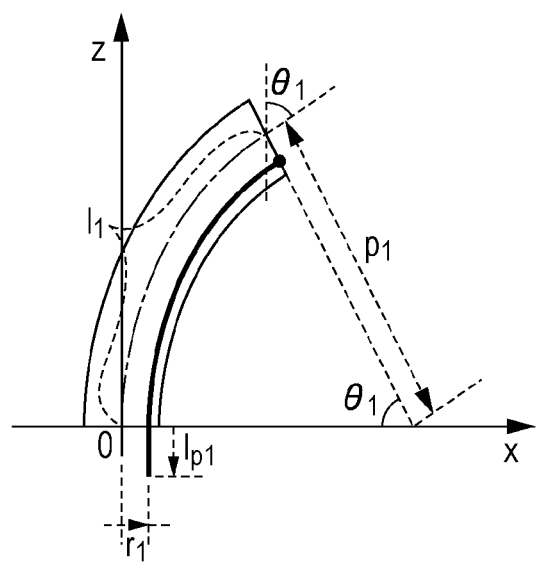

[Fig. 3]
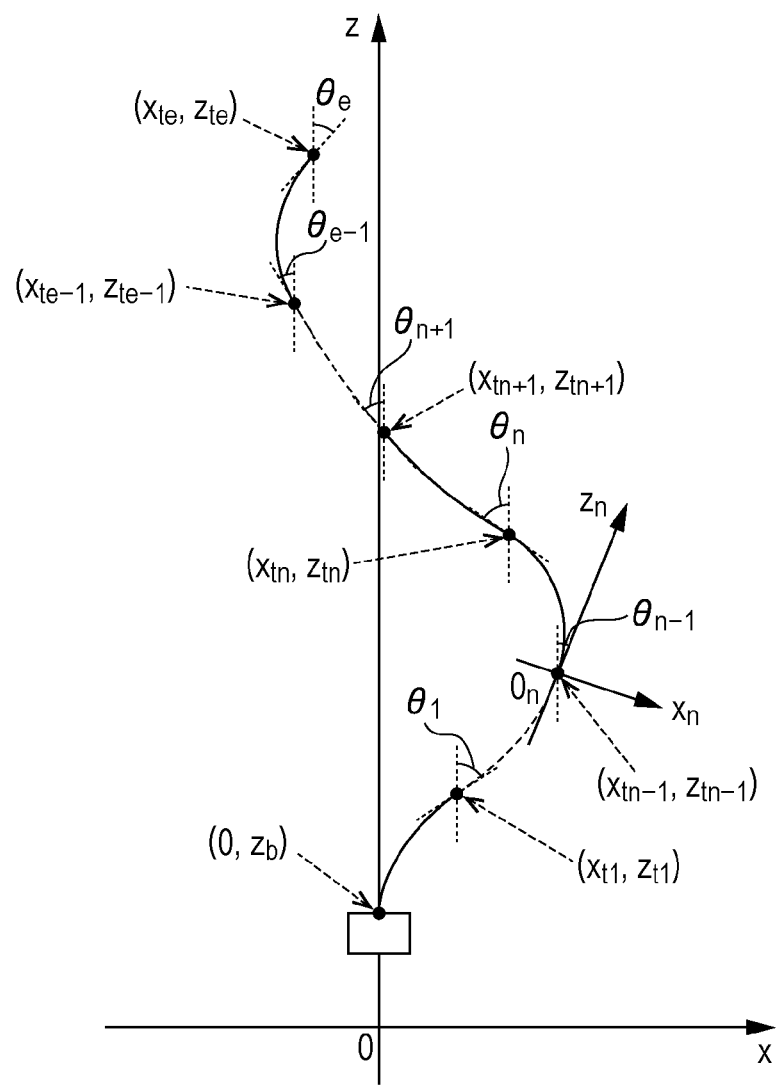

[Fig. 4]
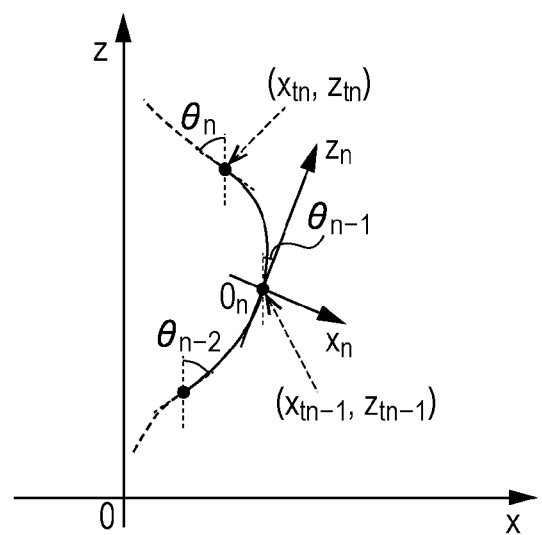

[Fig. 5]
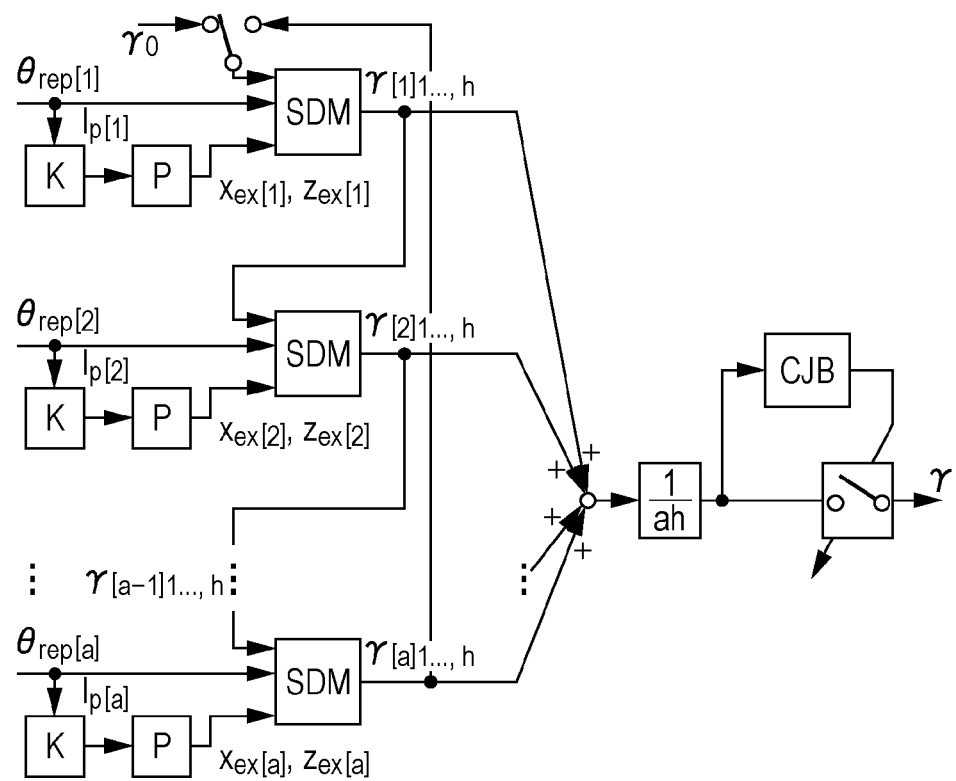

[Fig. 6]
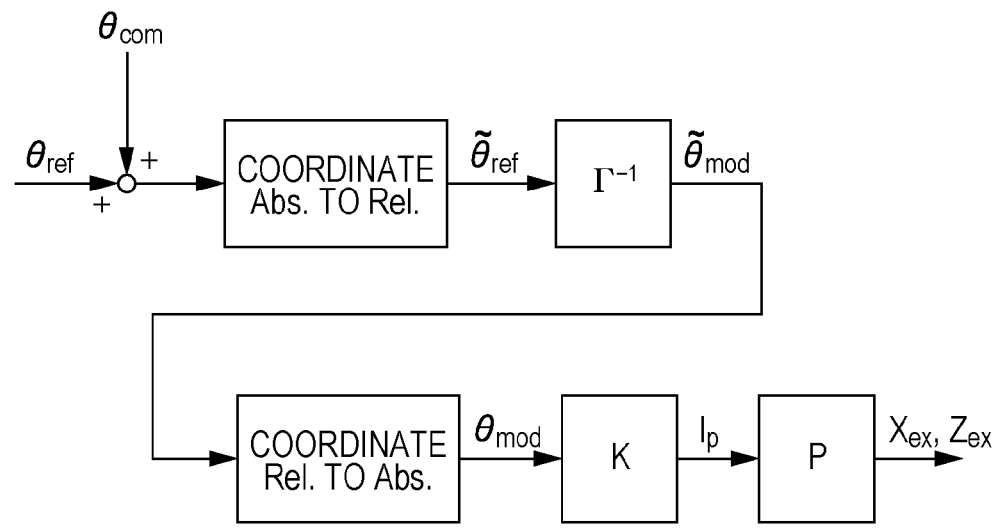

[Fig. 7]
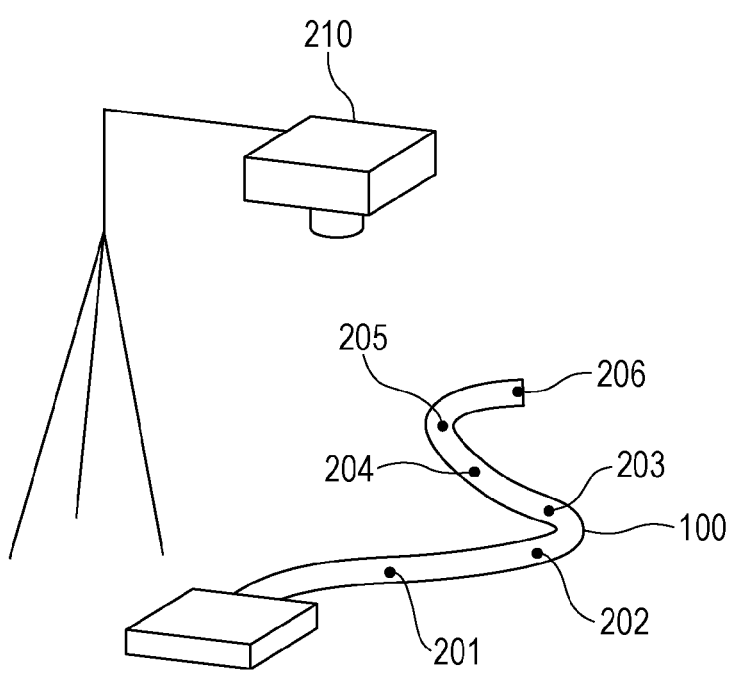

[Fig. 8A]
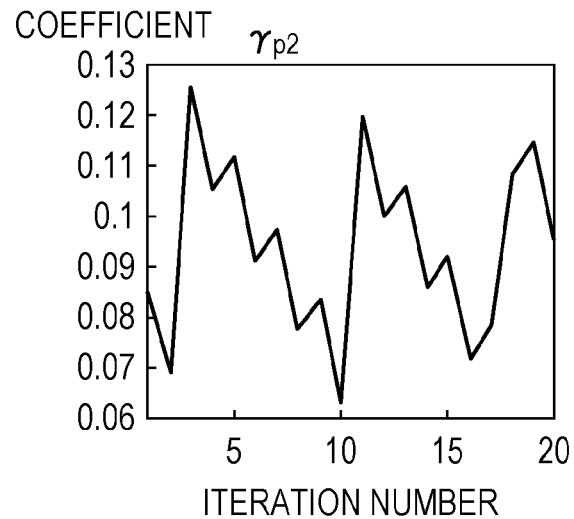
[Fig. 8B]
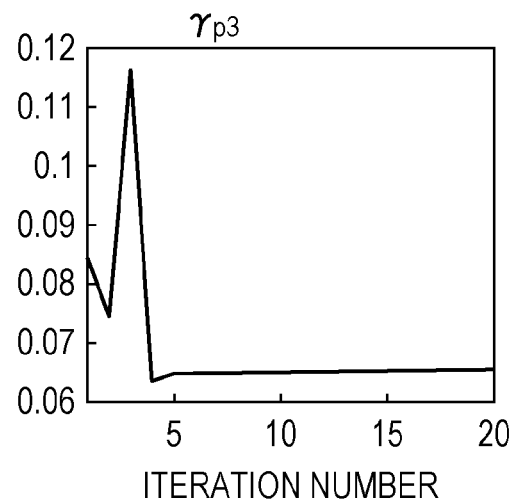
[Fig. 8C]
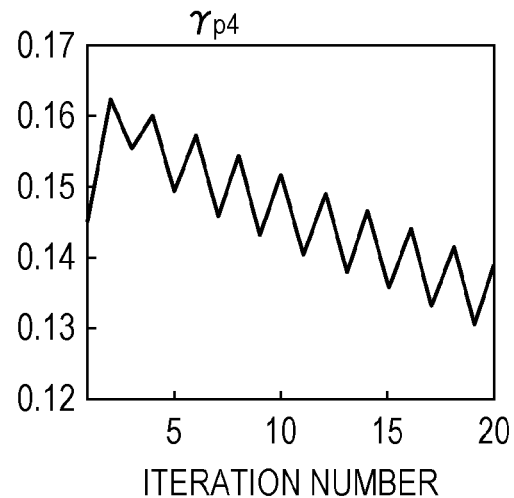

[Fig. 8D]
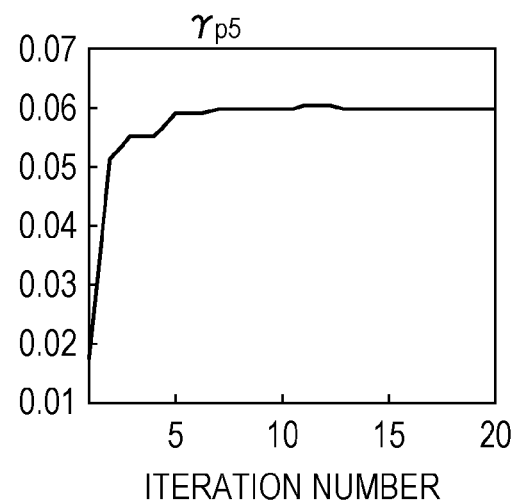
[Fig. 8E]
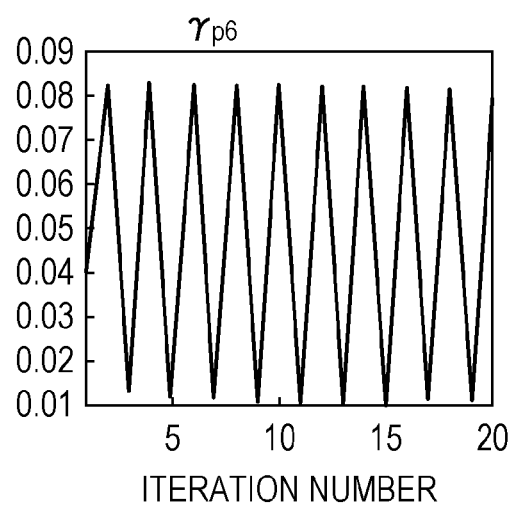

[Fig. 8F]
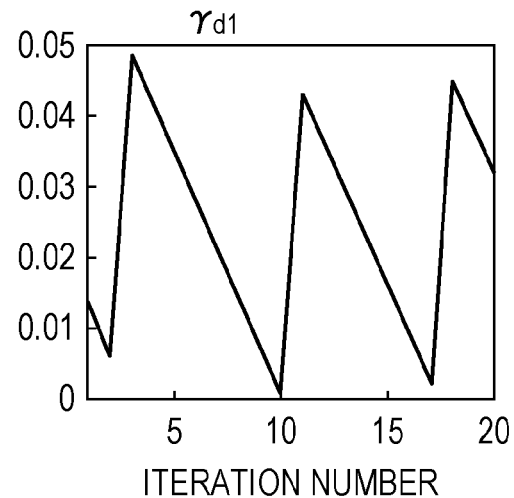
[Fig. 8G]
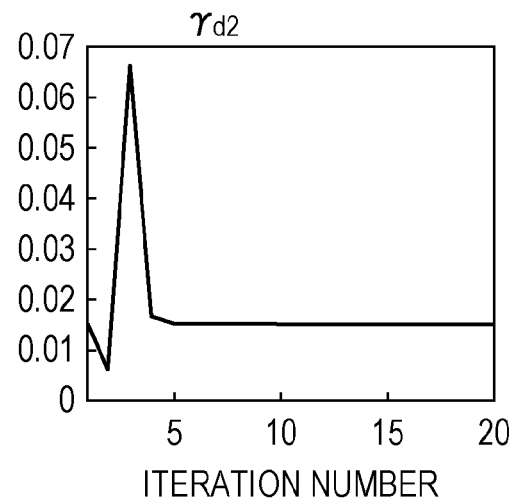
[Fig. 8H]
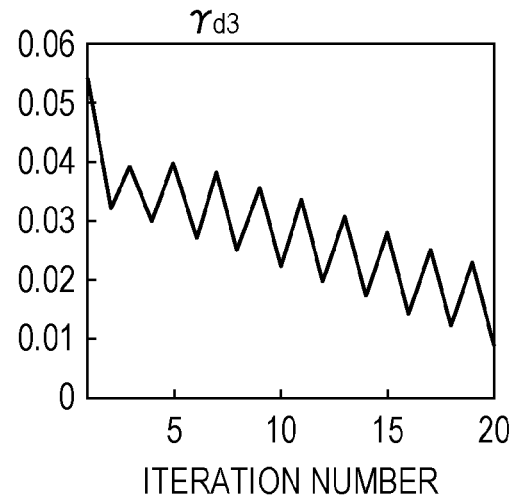

[Fig. 8I]
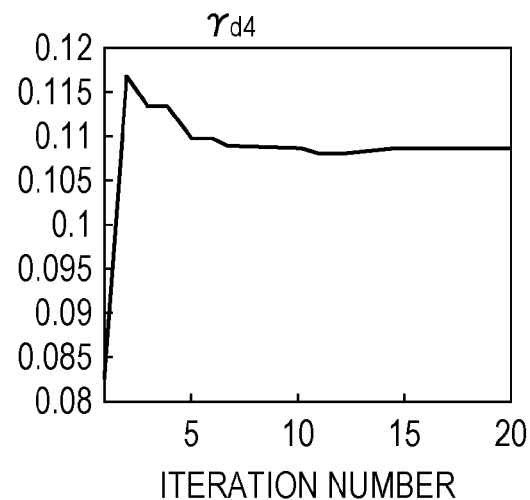
[Fig. 8J]
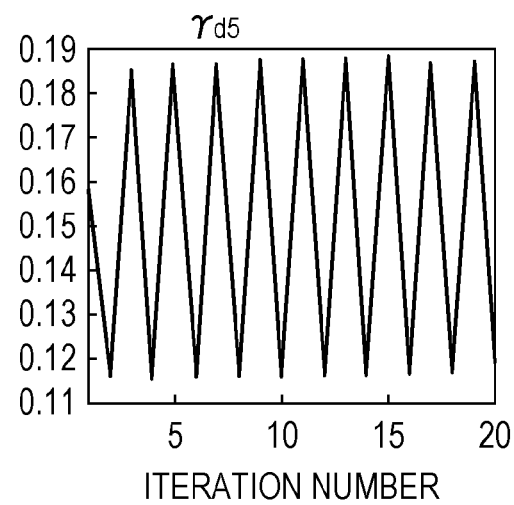

[Fig. 9A]
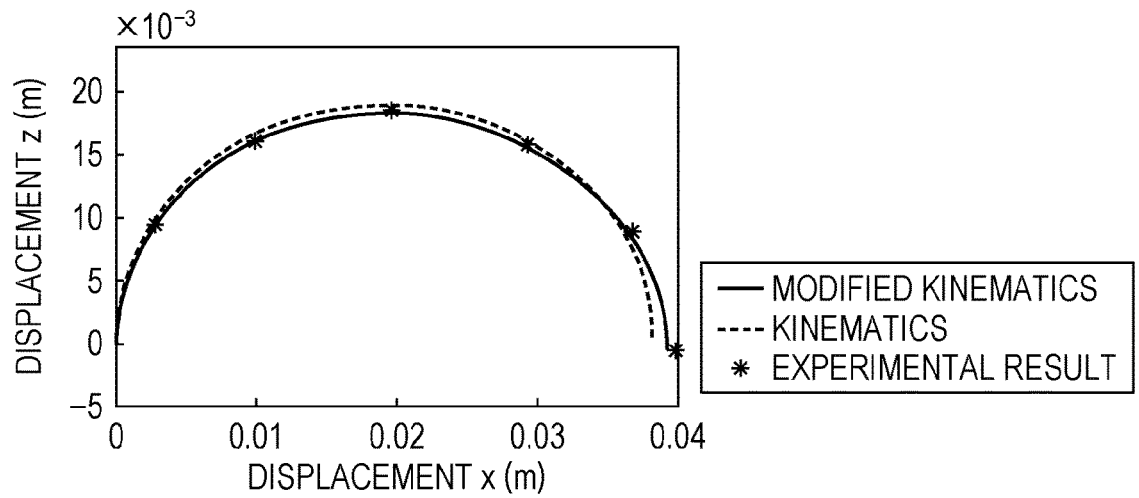
[Fig. 9B]
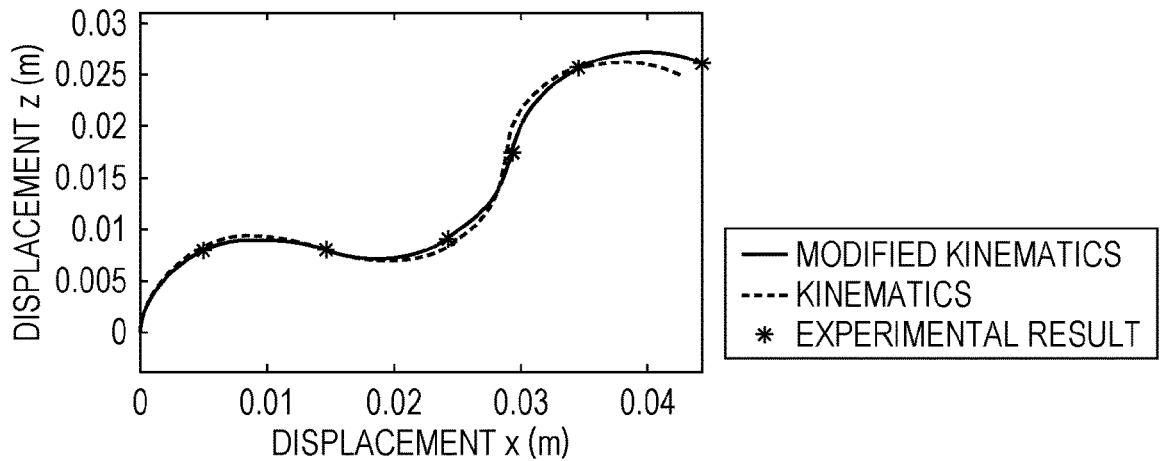
[Fig. 9C]
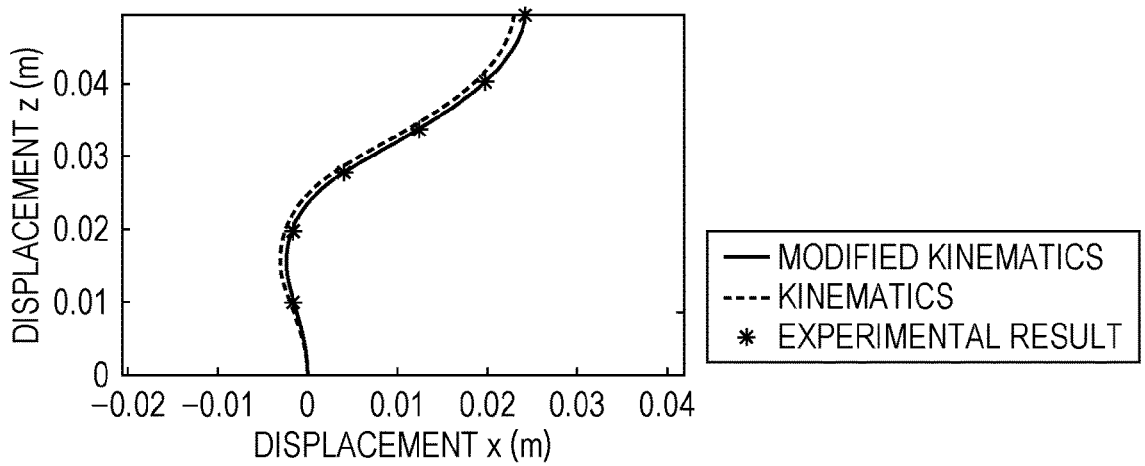

[Fig. 10A]
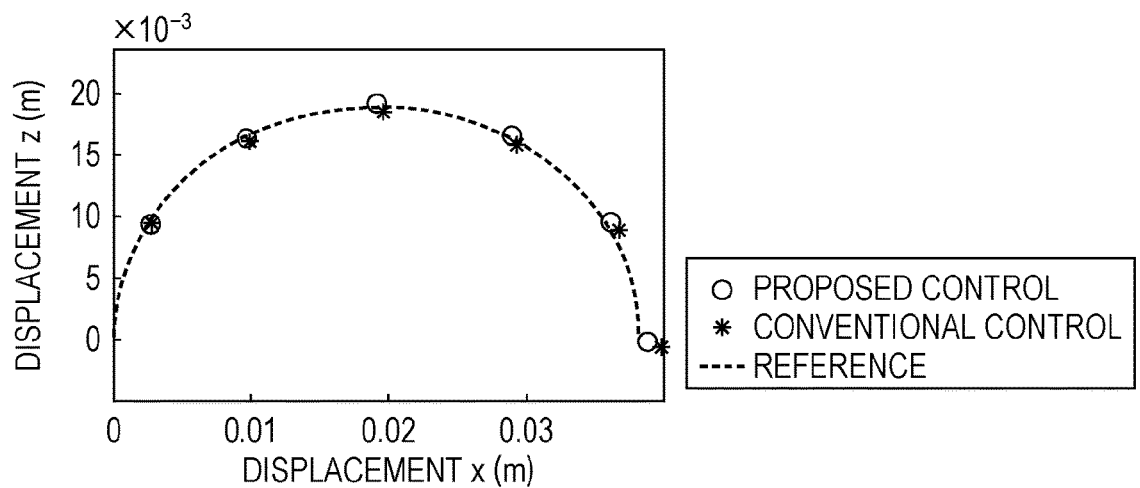
[Fig. 10B]
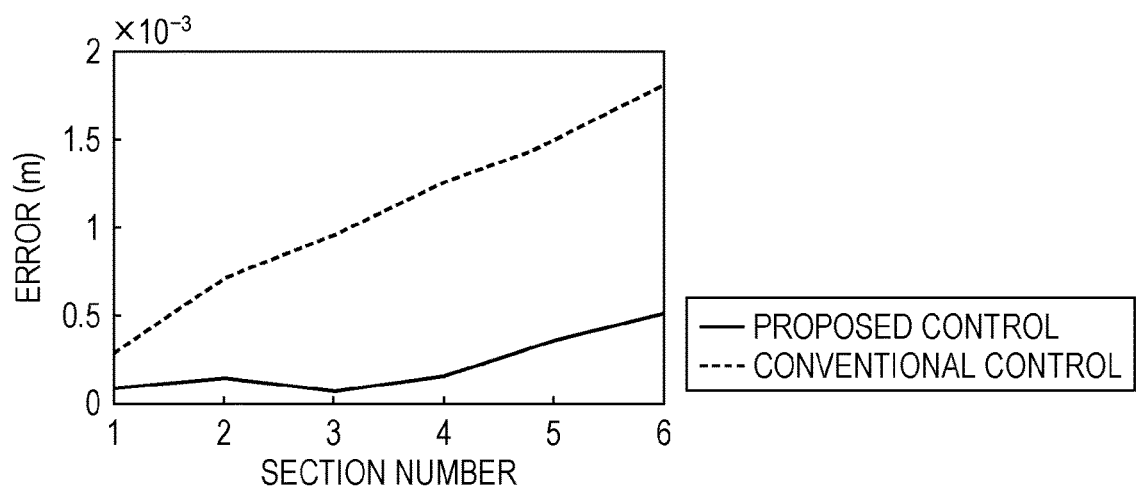

[Fig. 11A]
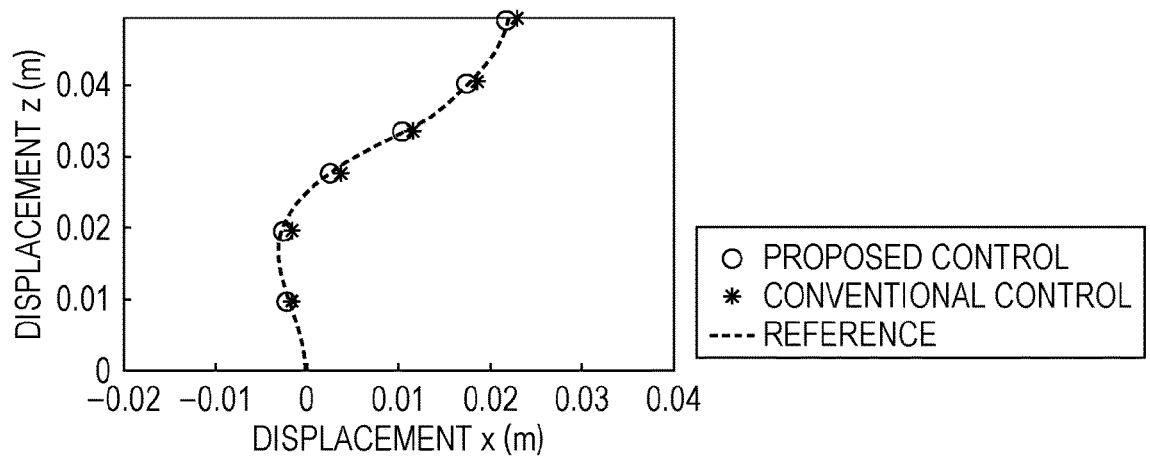
[Fig. 11B]
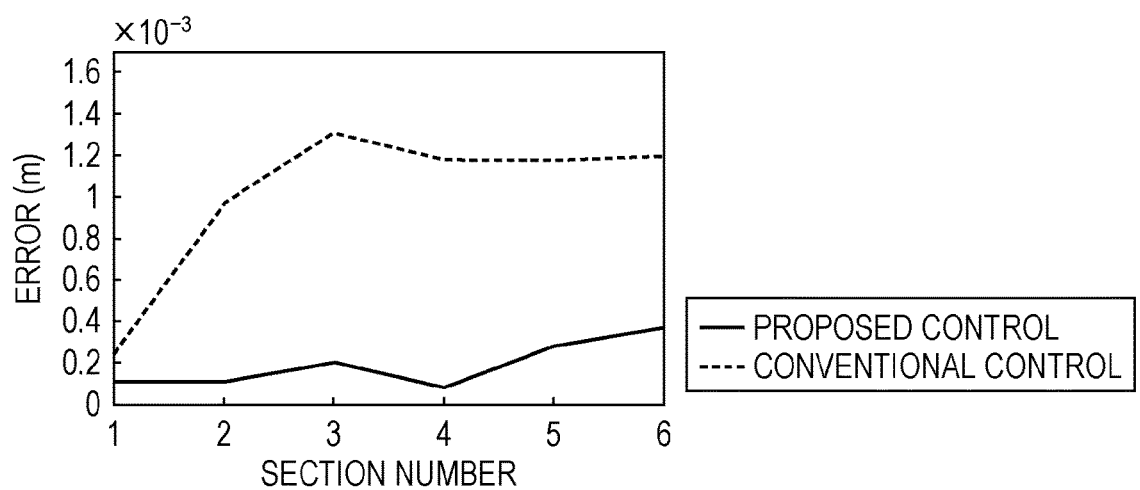

[Fig. 12]
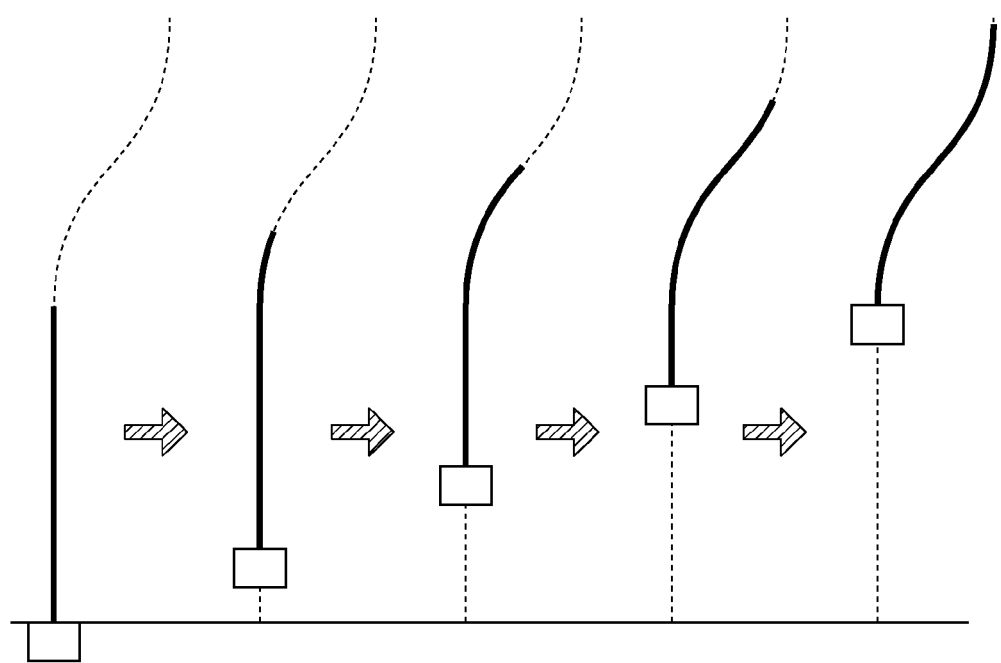

[Fig. 13]
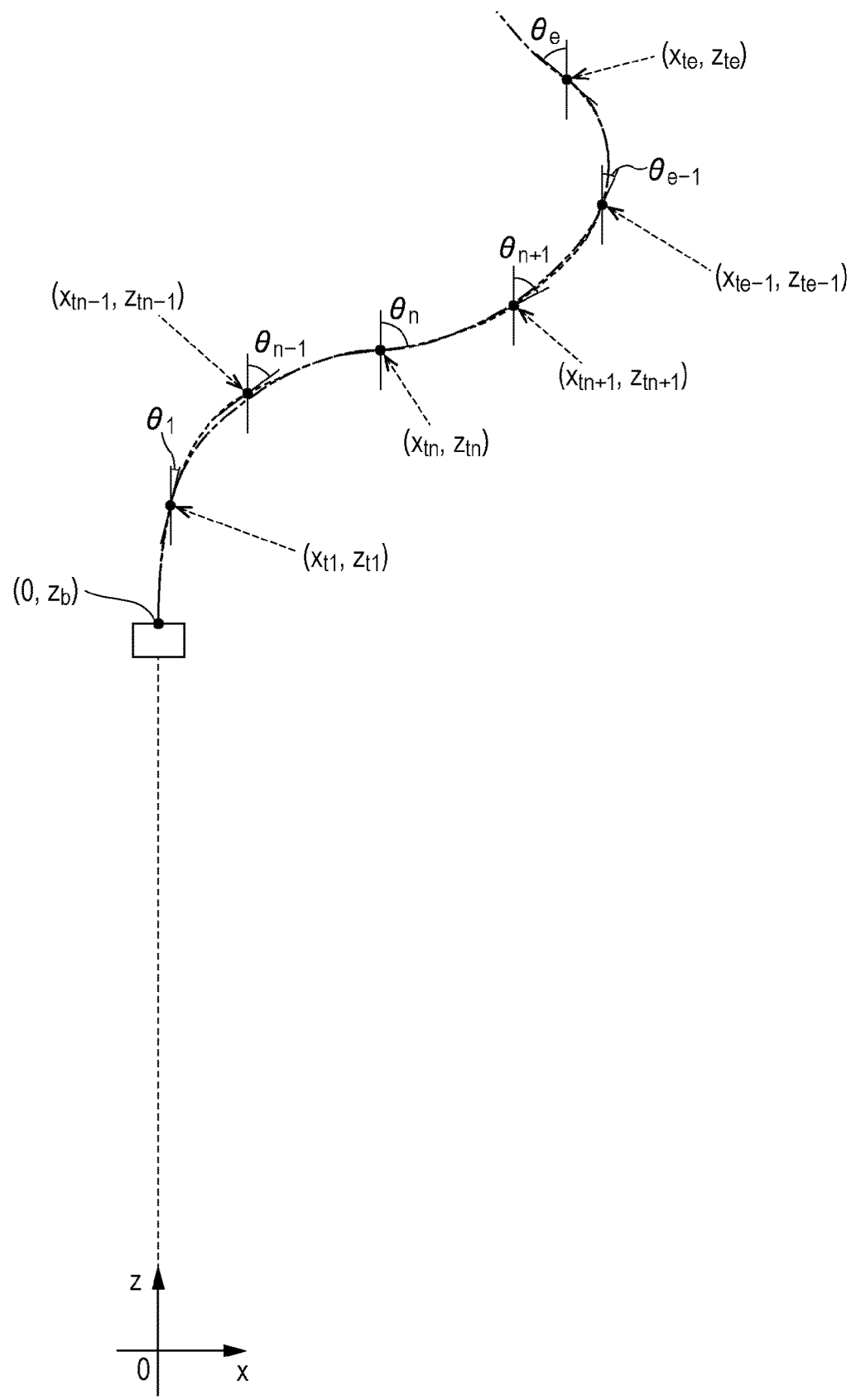

[Fig. 14]
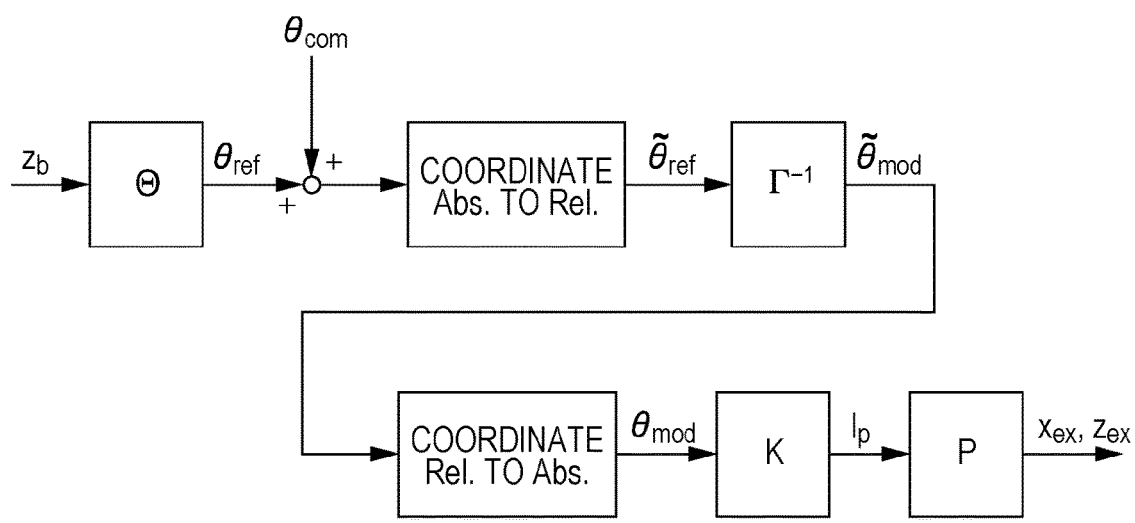

[Fig. 15A]
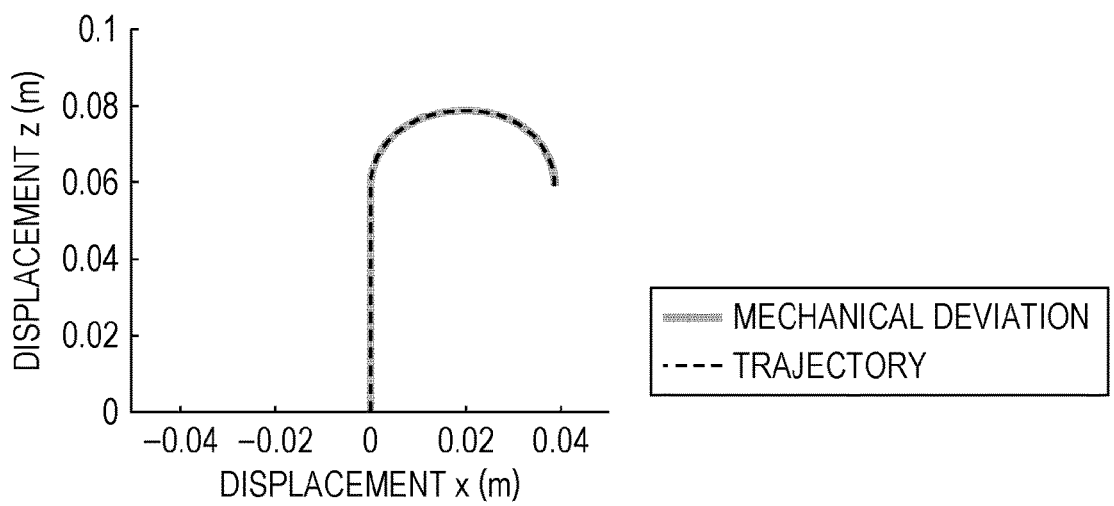
[Fig. 15B]
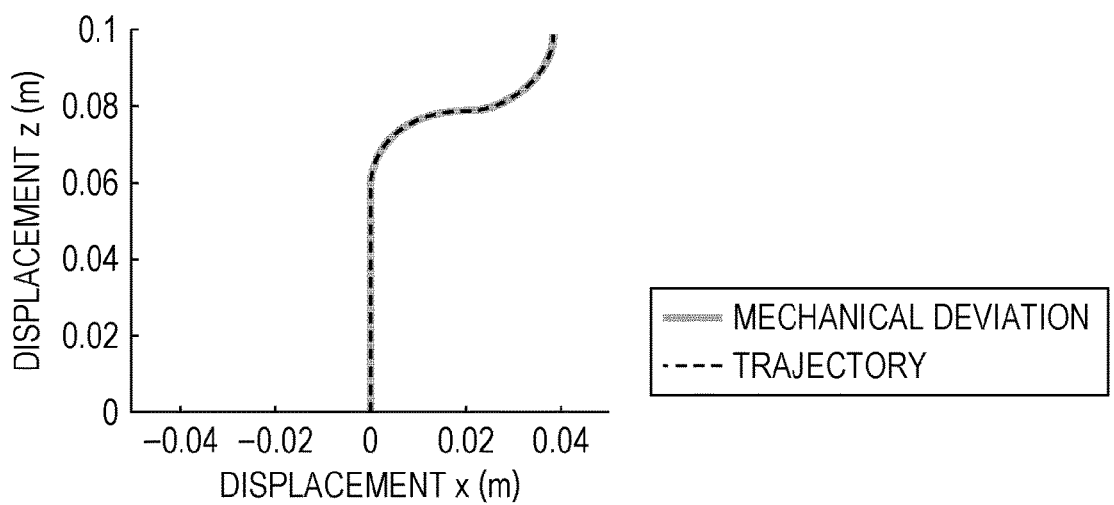

[Fig. 16A]
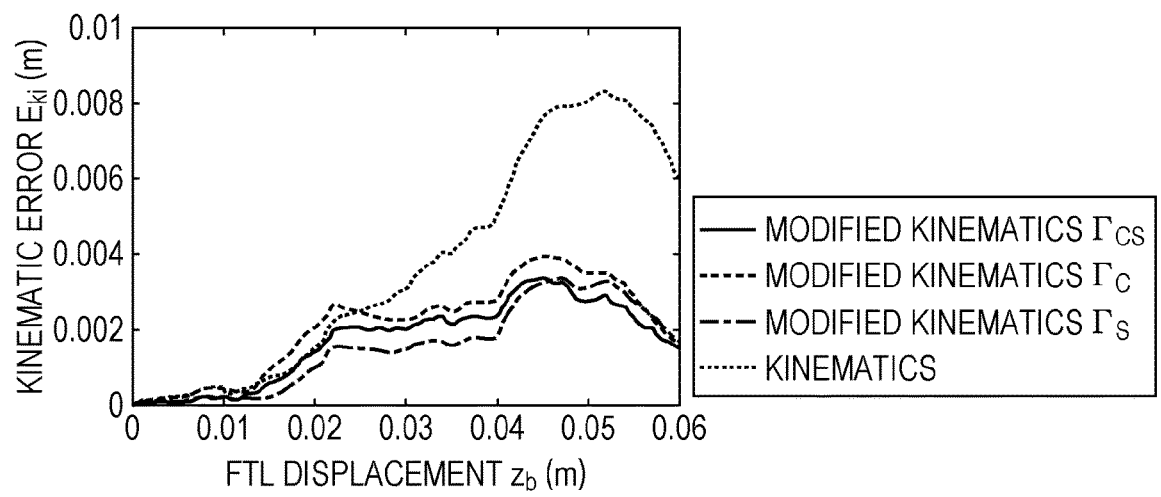
[Fig. 16B]
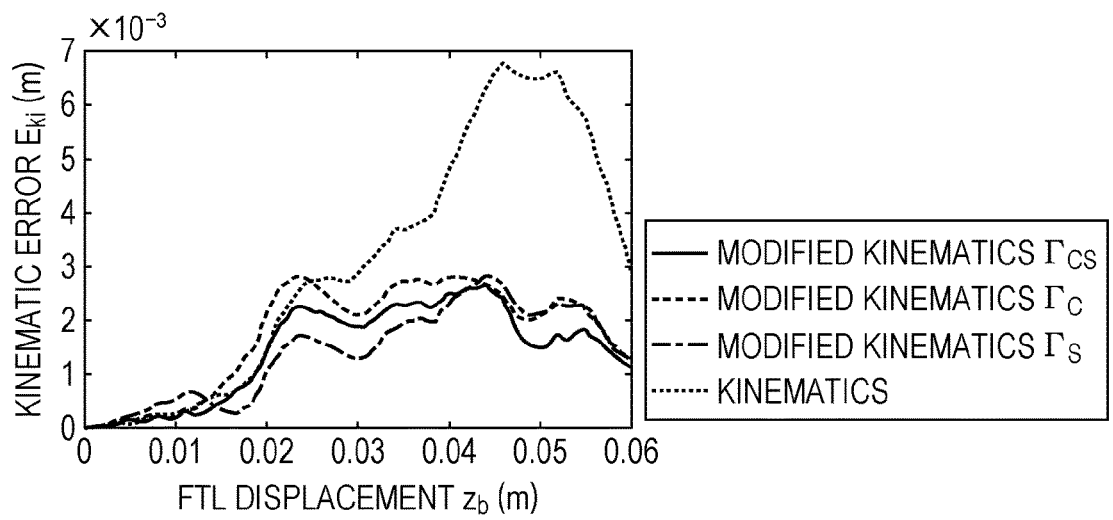

[Fig. 17]
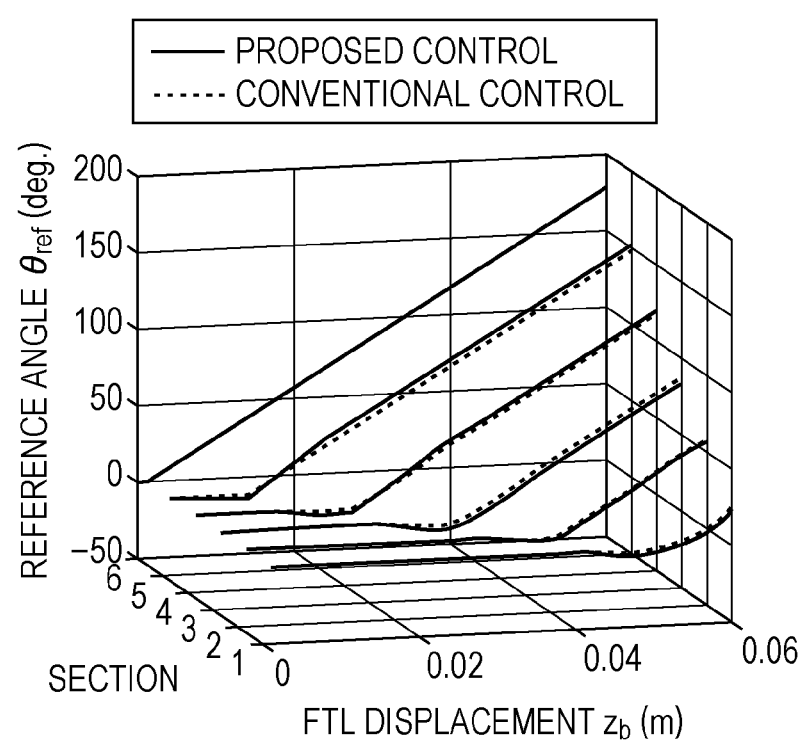

[Fig. 18A]
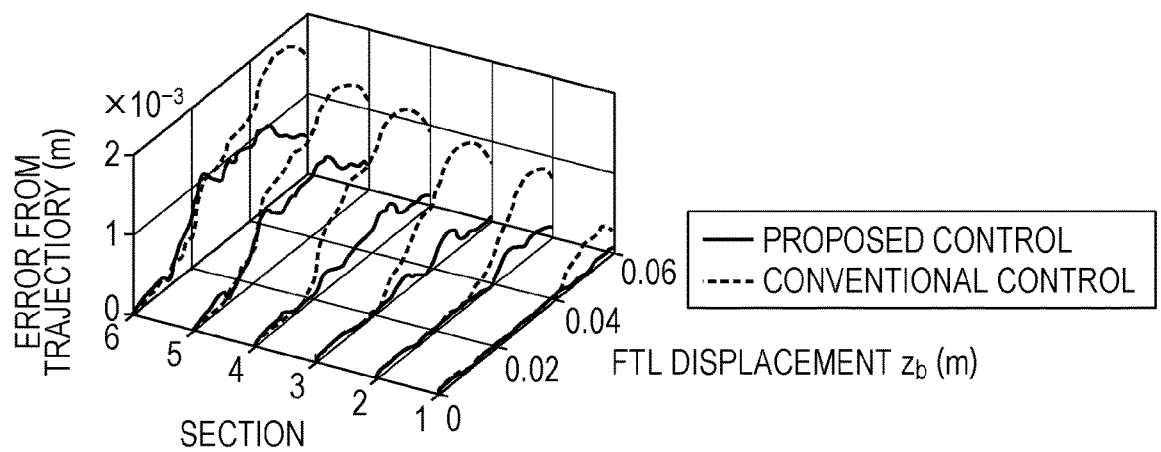
[Fig. 18B]
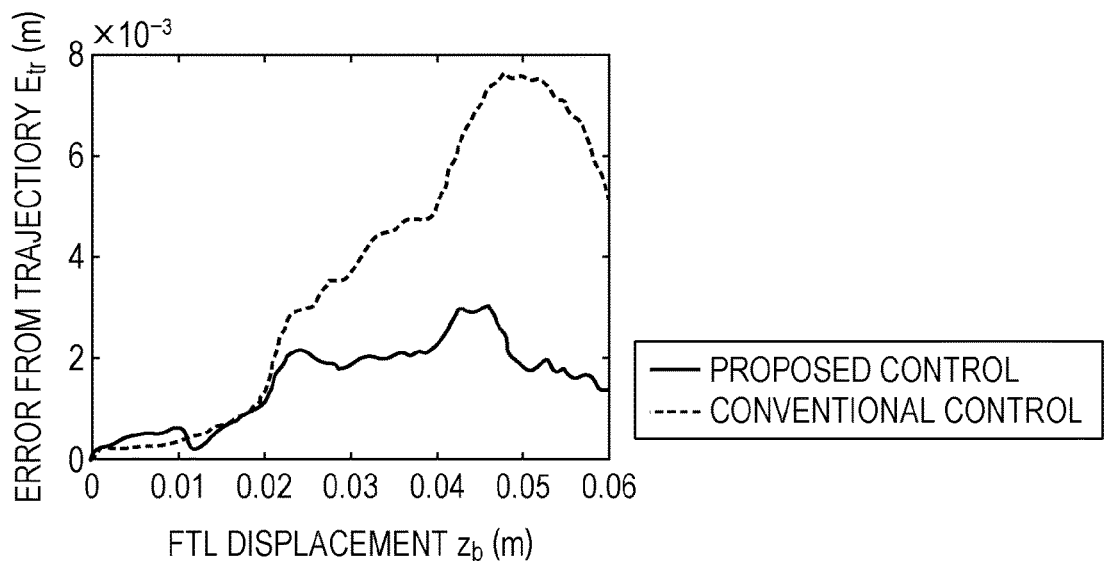

[Fig. 18C]
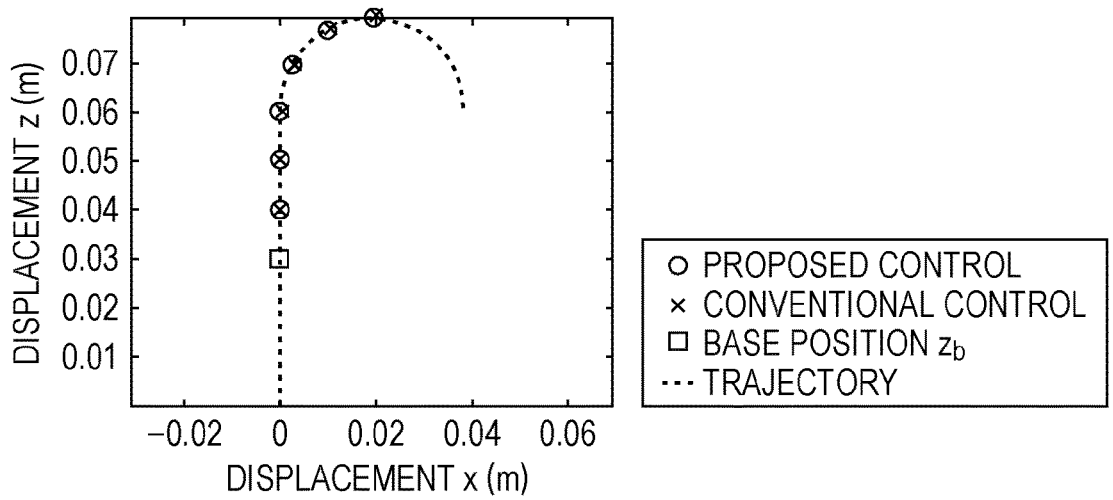
[Fig. 18D]
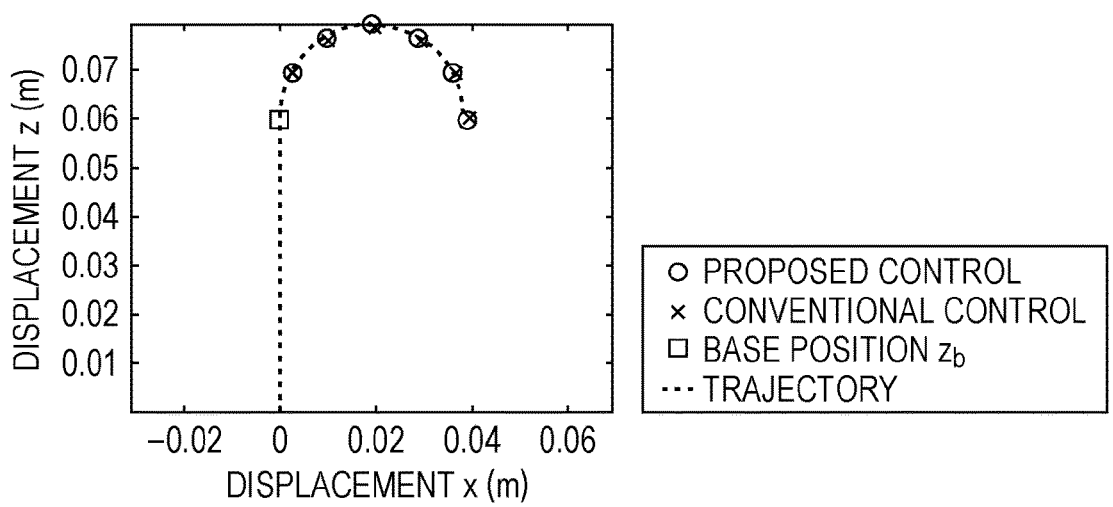

[Fig. 19A]
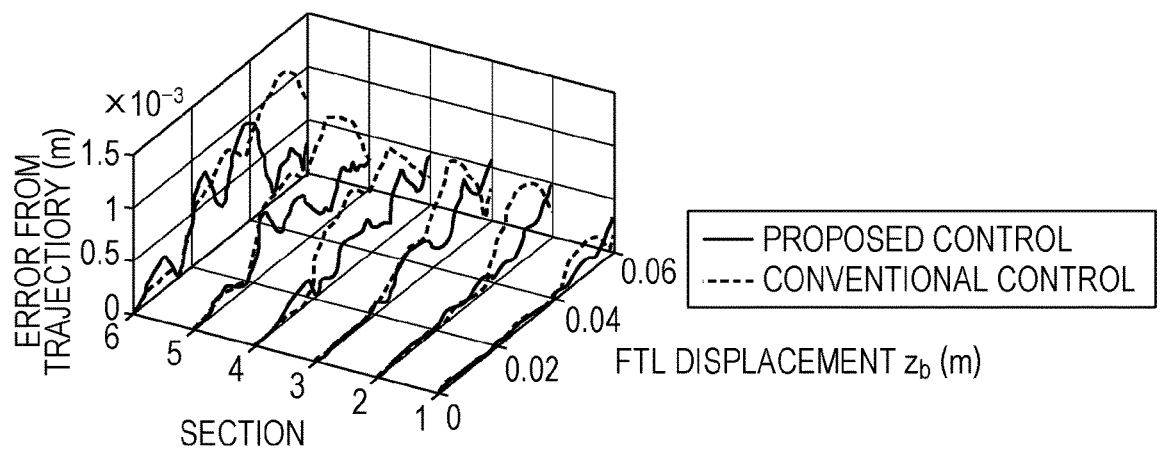
[Fig. 19B]
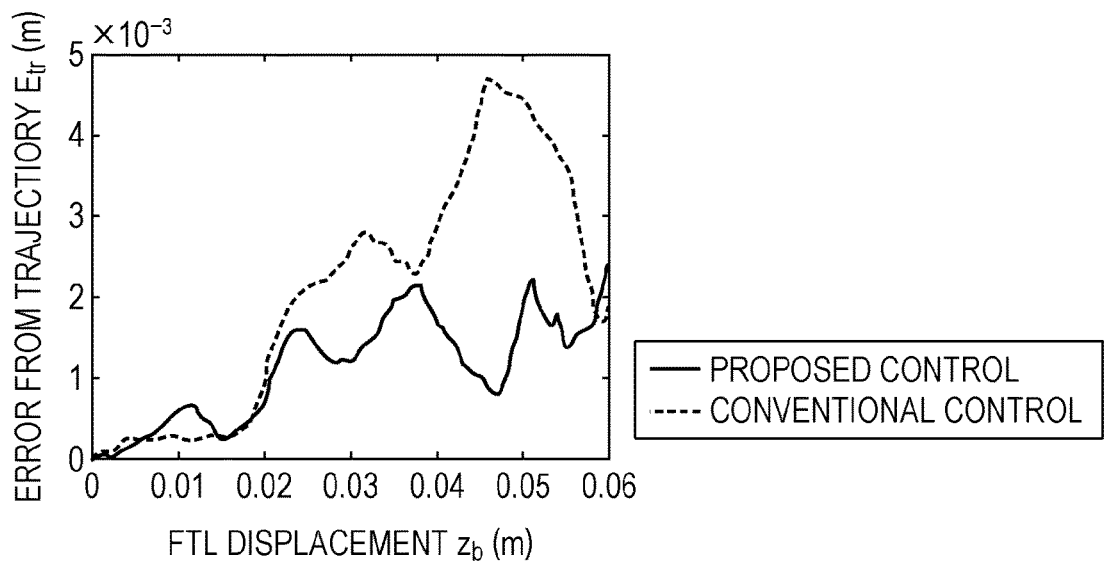

[Fig. 19C]
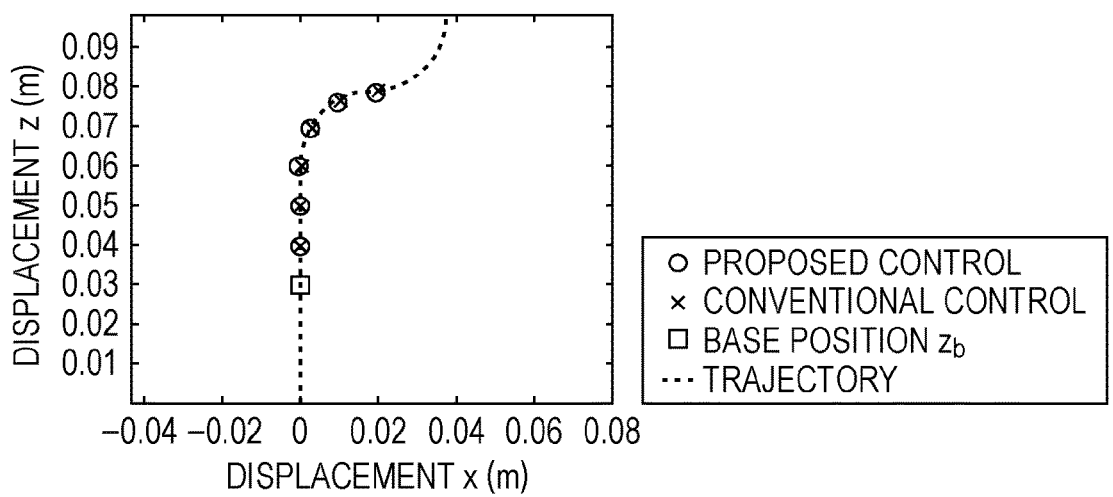
[Fig. 19D]
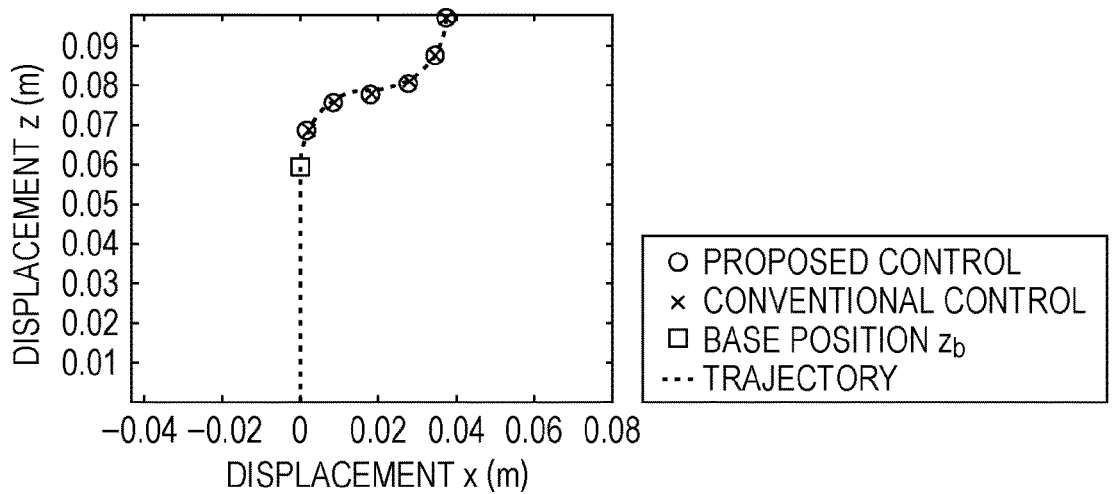

[Fig. 20]
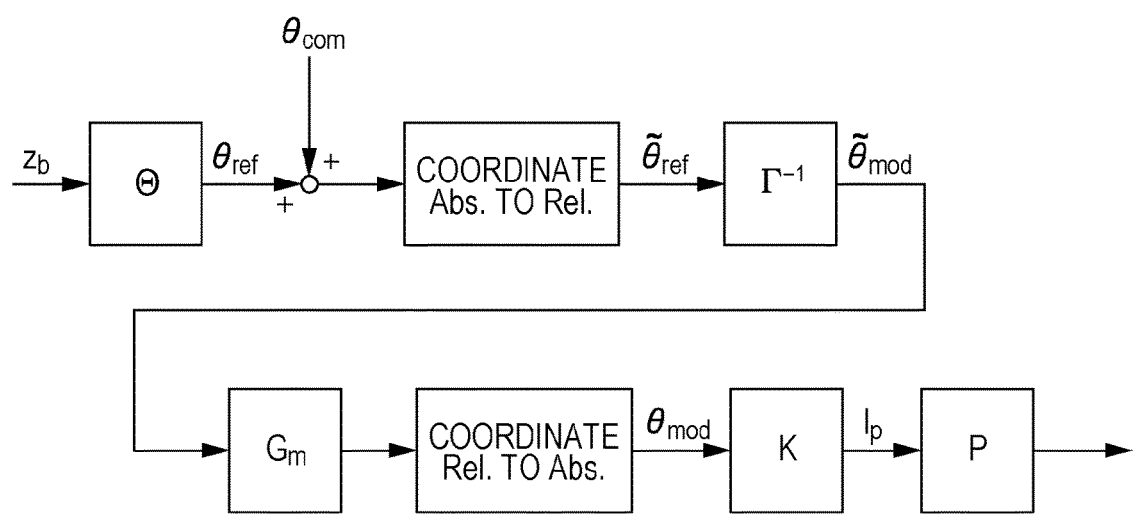

[Fig. 21A]
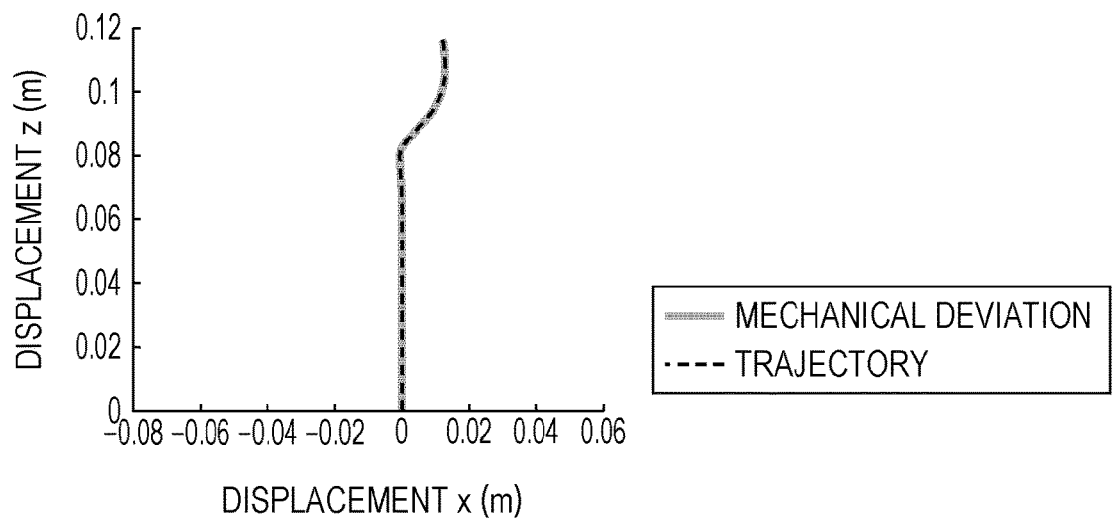
[Fig. 21B]
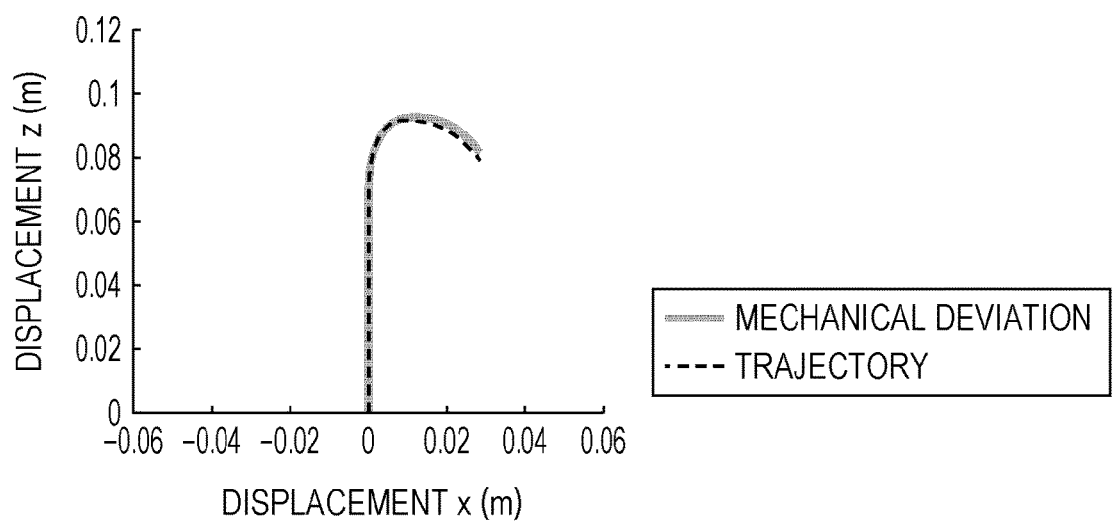

[Fig. 22A]
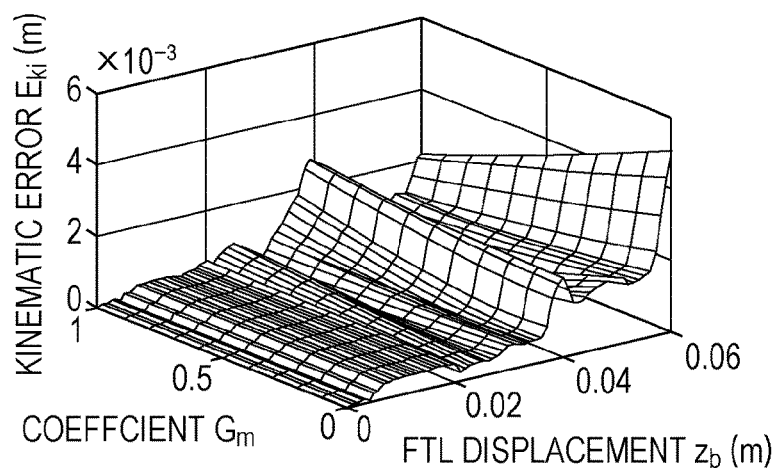
[Fig. 22B]
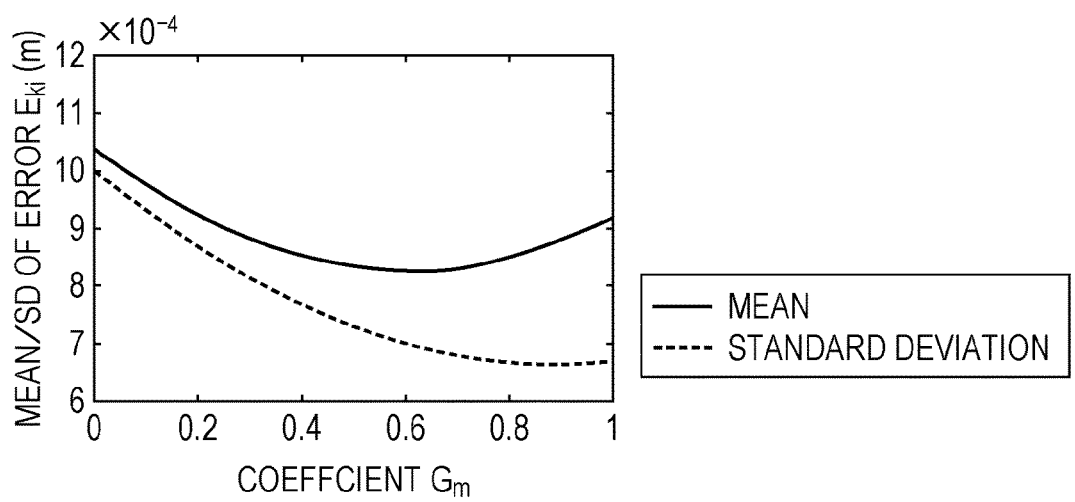

[Fig. 23A]
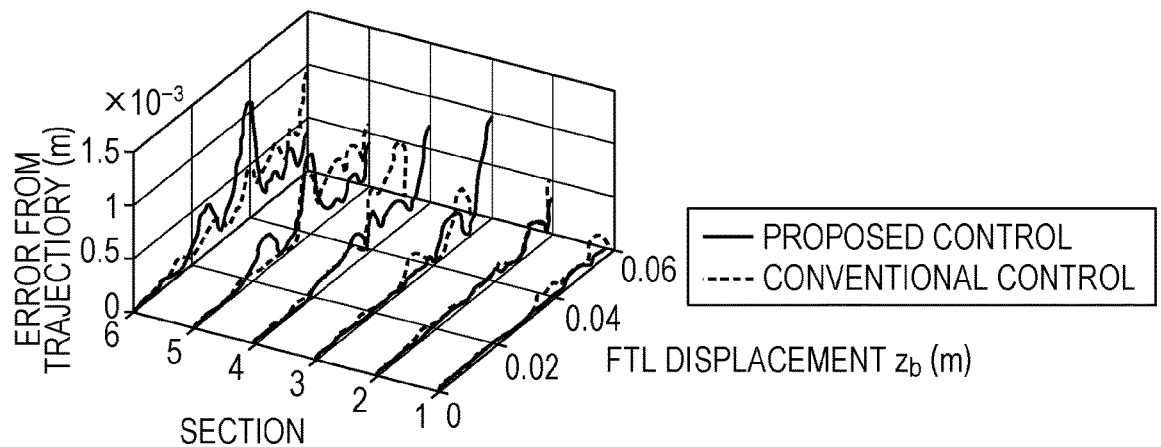
[Fig. 23B]
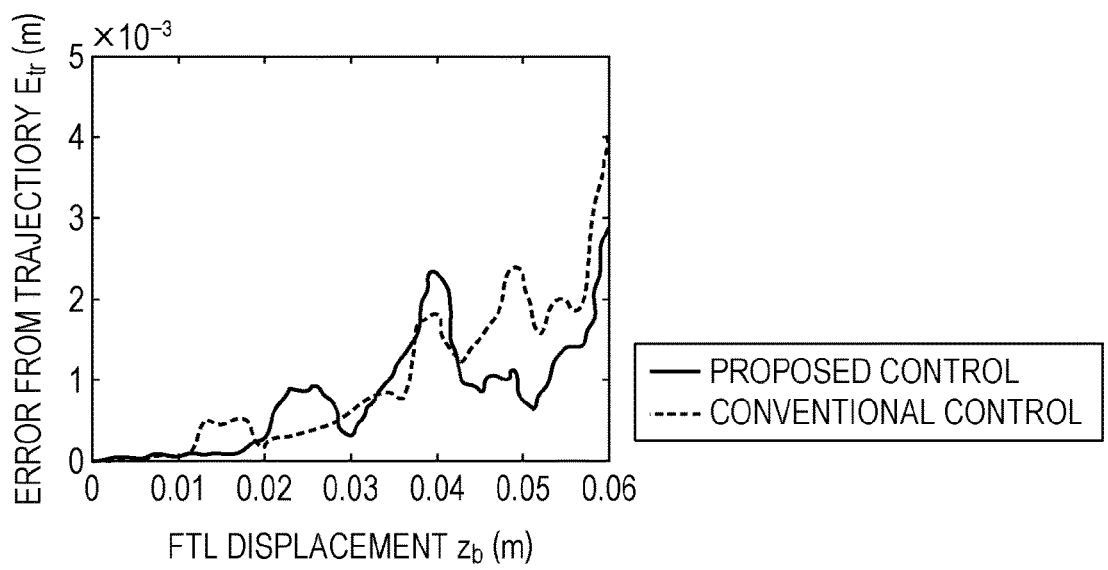

[Fig. 23C]
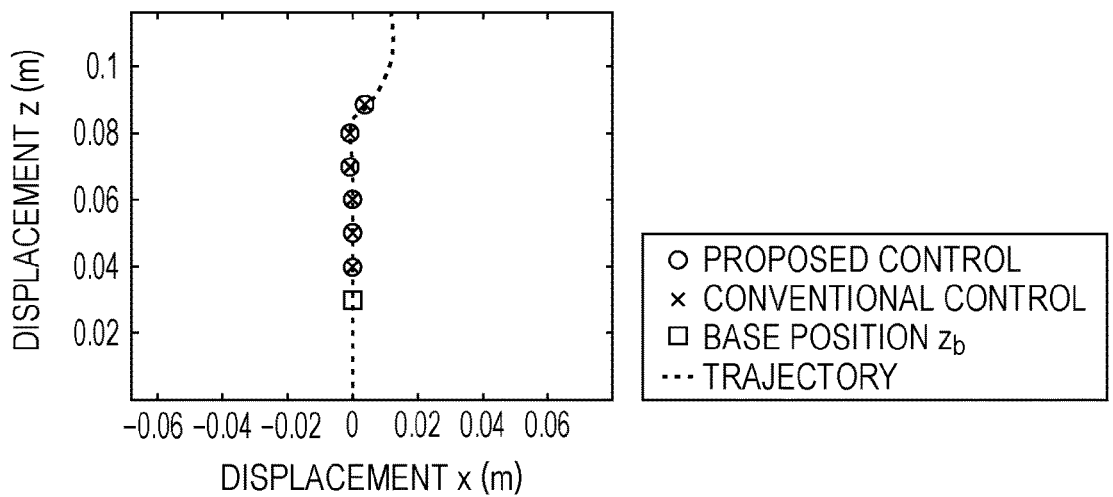
[Fig. 23D]
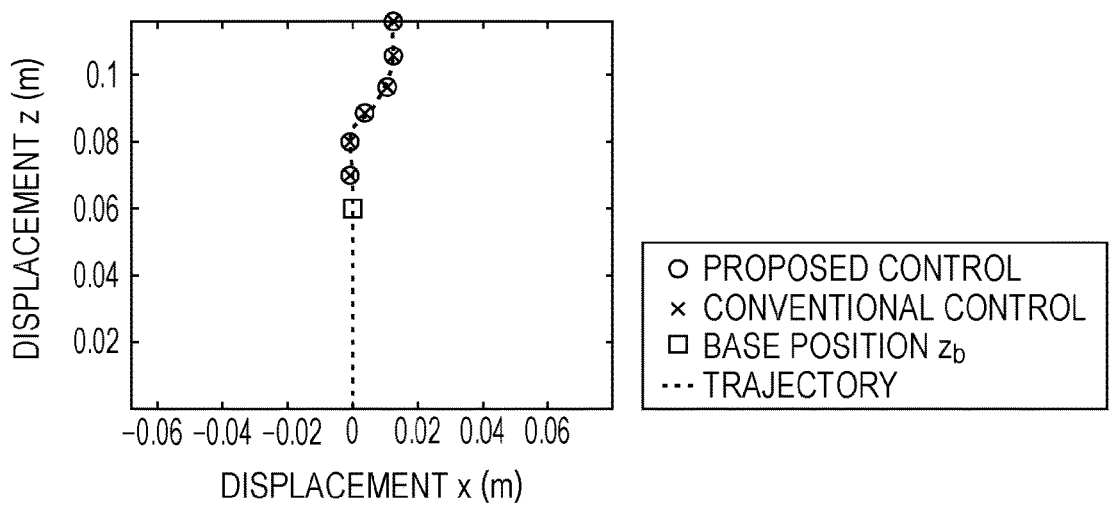

[Fig. 24A]
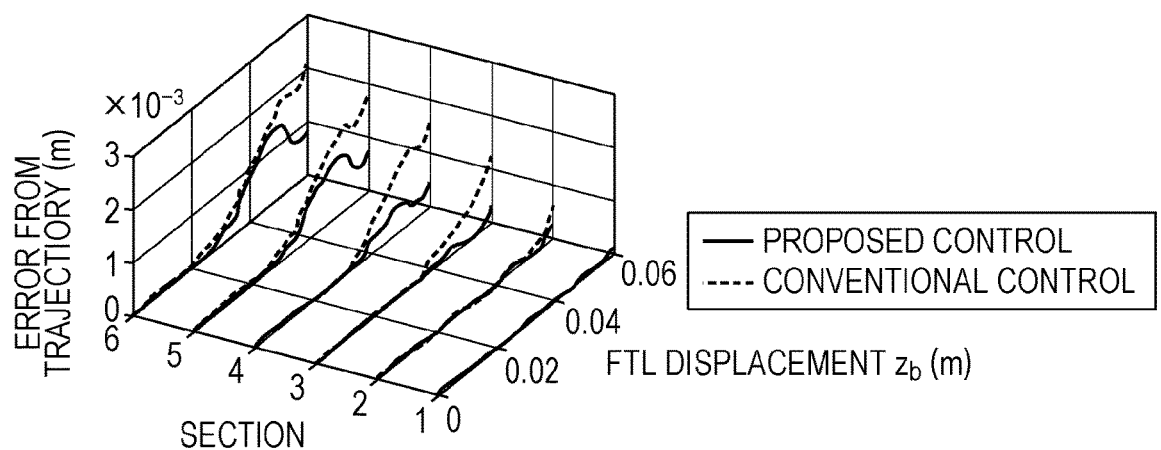
[Fig. 24B]
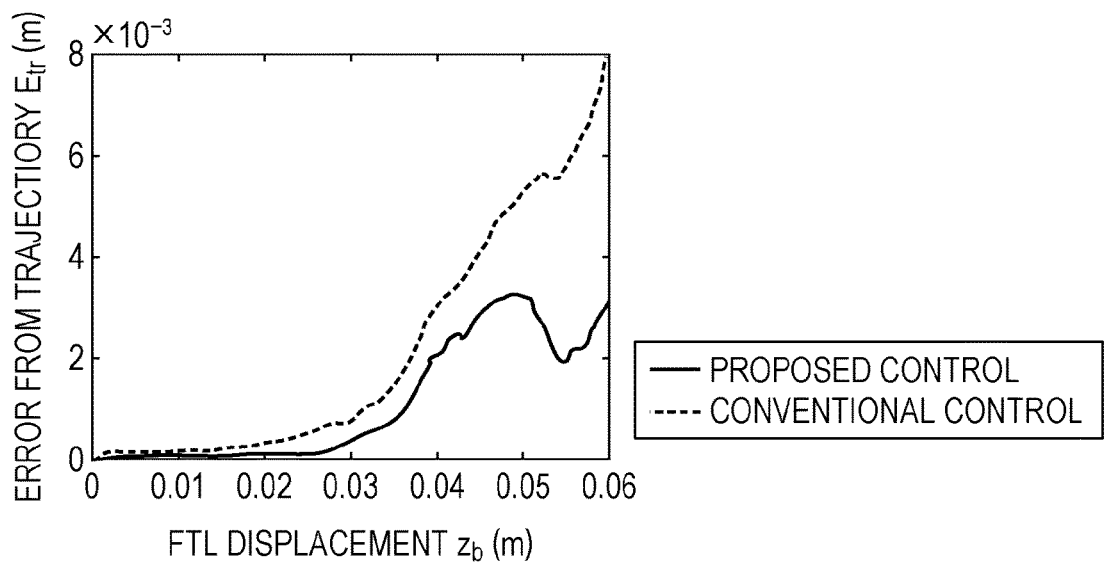

[Fig. 24C]
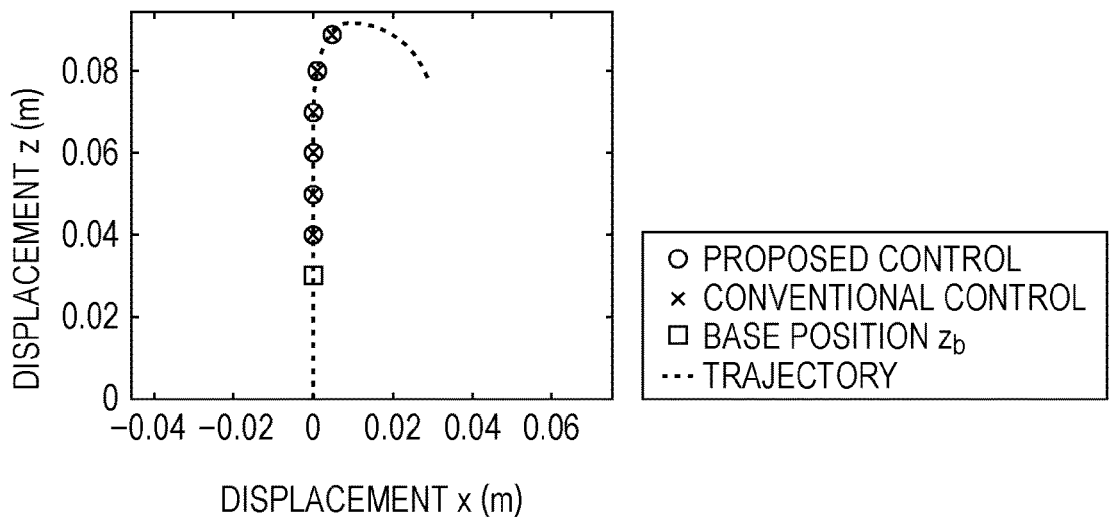
[Fig. 24D]
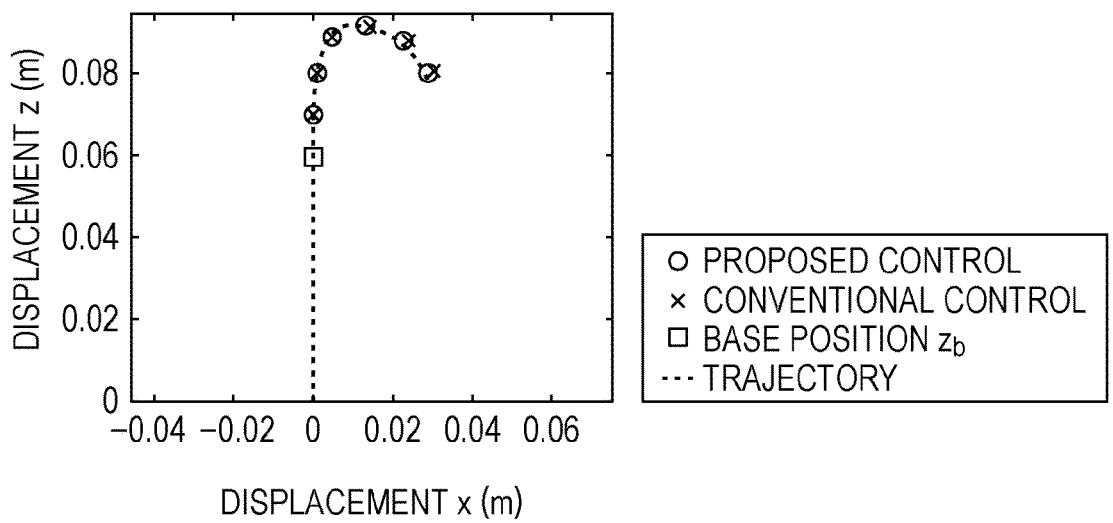

US 11,331,797 B2

CONTINUUM ROBOT, MODIFICATION METHOD OF KINEMATIC MODEL OF CONTINUUM ROBOT, AND CONTROL METHOD OF CONTINUUM ROBOT

CROSS-REFERENCE TO RELATED APPLICATIONS

This application is a National Phase application of International Application No. PCT/JP2017/024599, filed Jul. 5, 2017, which claims the benefit of Japanese Patent Application No. 2016-138133, filed Jul. 13, 2016. The disclosures of the above-named applications are hereby incorporated by reference herein in their entirety.

TECHNICAL FIELD

The present disclosure relates to a continuum robot, a modification method of a kinematic model of the continuum robot, and a control method of the continuum robot.

BACKGROUND ART

A continuum robot consists of a plurality of curvable sections (curvable portions) of a flexible structure, and an entire shape thereof is controlled by transforming or moving the curvable sections. This robot is superior to robots constituted by rigid links in two respects. First, a continuum robot is movable along a curve in a narrow space or in an environment with scattered objects where a robot with rigid links may become stuck. Second, since a continuum robot is essentially flexible, the robot can be operated without damaging a vulnerable target object. Therefore, detection of external force needed in a case where a robot with rigid links is used may become unnecessary. According to this feature, application of the continuum robot to the medical field, such as for a sheath of an endoscope or a catheter, and to hazardous environments, such as for rescue robots, is expected. However, since the continuum robot has an infinite degree of freedom due to its flexible structure, derivation of a kinematic model thereof is difficult. That is, it is not easy, when data of target positions in curvable sections is provided, to derive a process to appropriately calculate a driving amount of an actuator and to present the ways in which the curvable sections are to be driven to implement the target position.

NPL 1 describes derivation of a kinematic model in which the curvature of curvable sections is assumed to be piecewise constant. This method is applied to many continuum robots. It is also possible to calculate a driving amount of an actuator for shape control by using this kinematic model. Further, in the technology disclosed in PTL 1, in order to derive a kinematic model and to modify an error thereof, precision in positioning control is improved by performing feedback control in curvable sections by using displacement and angle sensors provided at ends of the curvable sections.

CITATION LIST

Patent Literature

PTL 1: U.S. Patent Application Publication No. 2013/0300537

Non Patent Literature

NPL 1: Design and Kinematic Modeling of Constant Curvature Continuum Robots: A Review, Robert J. Webster III and Bryan A. Jones, The international Journal of Robotics Research 29(13) 1661-1683

SUMMARY OF INVENTION

Technical Problem

However, the approach using the kinematic model described in NPL 1 does not consider modeling errors, such as friction and twisting of the robot, or extension and contraction of wires used as actuators, and precision in shape control may be lowered by the errors. In PTL 1, positions of three curvable sections are compensated by using magnetic sensors, however, there is an issue that installation of the magnetic sensors is difficult in a narrow-diameter continuum robot. Further, for the magnetic sensors it is necessary that a detection system be installed outside of the continuum robot, which may limit the use of the continuum robot.

Solution to Problem

A continuum robot of an aspect of the present disclosure includes a control method of a continuum robot, which includes a first curvable portion capable of curving, at least one second curvable portion provided adjacent to the first curvable portion and capable of curving, a first wire connected to the first curvable portion, and a second wire connected to the second curvable portion, a control unit configured to control curves of the first curvable portion and the second curvable portion by controlling driving of the first wire and the second wire, wherein the control unit controls driving of the first wire and the second wire on the basis of a kinematic model in consideration of a curve of the second curvable portion accompanying driving of the first wire in order to curve the first curvable portion and a curve of the first curvable portion accompanying driving of the second wire in order to curve the second curvable portion. Alternatively, the control unit controls driving of the first wire and the second wire so that a curve target value of the first curvable portion is achieved by the sum of curved amounts of the first curvable portion and the second curvable portion.

A modification method of a kinematic model of a continuum robot of another aspect of the present disclosure includes modifying the kinematic model by using a model in consideration of a curve of the second curvable portion accompanying driving of the first wire in order to curve the first curvable portion and a curve of the first curvable portion accompanying driving of the second wire in order to curve the second curvable portion. Alternatively, the kinematic model is modified by using a model for controlling driving of the first wire and the second wire so that a curve target value of the first curvable portion is achieved by the sum of curved amounts of the first curvable portion and the second curvable portion.

A control method of a continuum robot of another aspect of the present disclosure includes obtaining a target position modified by multiplying data of the target position of the curvable portion by an inverse of a modification value by using a modification method in which a modification value for modifying a kinematic model which represents a relationship between data of a target position of the curvable portion and a position of the curvable portion by a driven displacement of the first wire and the second wire derived from the data in accordance with a mechanism of the continuum robot is obtained by an algorithm using an optimization technique to reduce an error between data of the target position of the curvable portion when the continuum robot obtains a predetermined curvature and a measurement value related to an actual position of the curvable portion, and controlling the curvable portion by a driven displacement of the wire calculated in accordance with the modified target position.

Advantageous Effects of Invention

According to an aspect of the present disclosure, an error with respect to a target position of a curvable portion of a continuum robot can be reduced by modifying a driving amount of an actuator obtained when data of the target position of the curvable portion of the continuum robot is provided.

Further features of the present invention will become apparent from the following description of exemplary embodiments with reference to the attached drawings.

BRIEF DESCRIPTION OF DRAWINGS

FIG. 1 illustrates an apparatus according to a first embodiment.
FIG. 2 illustrates a kinematic model according to the first embodiment.
FIG. 3 illustrates a kinematic model according to the first embodiment.
FIG. 4 illustrates a kinematic model according to the first embodiment.
FIG. 5 is a block diagram illustrating an optimization algorithm according to the first embodiment.
FIG. 6 is a block diagram illustrating a control system according to the first embodiment.
FIG. 7 illustrates a displacement measurement apparatus according to the first embodiment.
FIG. 8A illustrates an experimental result according to the first embodiment.
FIG. 8B illustrates an experimental result according to the first embodiment.
FIG. 8C illustrates an experimental result according to the first embodiment.
FIG. 8D illustrates an experimental result according to the first embodiment.
FIG. 8E illustrates an experimental result according to the first embodiment.
FIG. 8F illustrates an experimental result according to the first embodiment.
FIG. 8G illustrates an experimental result according to the first embodiment.
FIG. 8H illustrates an experimental result according to the first embodiment.
FIG. 8I illustrates an experimental result according to the first embodiment.
FIG. 8J illustrates an experimental result according to the first embodiment.
FIG. 9A illustrates an experimental result according to the first embodiment.
FIG. 9B illustrates an experimental result according to the first embodiment.
FIG. 9C illustrates an experimental result according to the first embodiment.
FIG. 10A illustrates an experimental result according to the first embodiment.
FIG. 10B illustrates an experimental result according to the first embodiment.
FIG. 11A illustrates an experimental result according to the first embodiment.
FIG. 11B illustrates an experimental result according to the first embodiment.
FIG. 12 illustrates follow-the-leader control according to a second embodiment.
FIG. 13 illustrates a kinematic model according to the second embodiment.
FIG. 14 is a block diagram illustrating a control system according to the second embodiment.
FIG. 15A is a block diagram illustrating a trajectory and a mechanical error according to the second embodiment.
FIG. 15B is a block diagram illustrating a trajectory and a mechanical error according to the second embodiment.
FIG. 16A illustrates an experimental result according to the second embodiment.
FIG. 16B illustrates an experimental result according to the second embodiment.
FIG. 17 illustrates a control instruction according to the second embodiment.
FIG. 18A illustrates an experimental result according to the second embodiment.
FIG. 18B illustrates an experimental result according to the second embodiment.
FIG. 18C illustrates an experimental result according to the second embodiment.
FIG. 18D illustrates an experimental result according to the second embodiment.
FIG. 19A illustrates an experimental result according to the second embodiment.
FIG. 19B illustrates an experimental result according to the second embodiment.
FIG. 19C illustrates an experimental result according to the second embodiment.
FIG. 19D illustrates an experimental result according to the second embodiment.
FIG. 20 is a block diagram illustrating a control system according to a third embodiment.
FIG. 21A is a block diagram illustrating a trajectory and a mechanical error according to the third embodiment.
FIG. 21B is a block diagram illustrating a trajectory and a mechanical error according to the third embodiment.
FIG. 22A illustrates an optimization algorithm according to the third embodiment.
FIG. 22B illustrates an optimization algorithm according to the third embodiment.
FIG. 23A illustrates an experimental result according to the third embodiment.
FIG. 23B illustrates an experimental result according to the third embodiment.
FIG. 23C illustrates an experimental result according to the third embodiment.
FIG. 23D illustrates an experimental result according to the third embodiment.
FIG. 24A illustrates an experimental result according to the third embodiment.
FIG. 24B illustrates an experimental result according to the third embodiment.
FIG. 24C illustrates an experimental result according to the third embodiment.
FIG. 24D illustrates an experimental result according to the third embodiment.

DESCRIPTION OF EMBODIMENTS

In the present disclosure, a kinematic model can be modified by using a model in consideration of continuity between curvable portions, and a continuum robot can be configured and a control method of a continuum robot can be configured in accordance with the modified kinematic model. In the control method, a corresponding one of the curvable portions is controlled by obtaining a driving amount of an actuator to obtain a target position by using data of the target position of the curvable portion (a curve target value) and an inverse of a modification value (a value which yields 1 when multiplied by a modification value) in the modified kinematic model. Not only control of a curved amount, which is previously set, but also real-time control of a curvature by real-time operation can be performed by sequentially adding additional target values of curvatures to the curve target value. This technology enables a control known as follow-the-leader control, and follow-the-leader control with respect to a trajectory with a non-constant curvature can also be performed by multiplying an inverse of the modification value by an additional gain.

First Embodiment

In a first embodiment, there is described a method for modifying the kinematic model described above by introducing a model of continuity between adjacent curvable sections, the shape of which is caused by a plurality of mechanical factors in addition to a kinematic model in which the curvature of curvable sections which are curvable portions is assumed to be piecewise constant. Further, an approach of improving driving and control of a continuum robot by the method will be described. A kinematic model of the continuum robot presents the position of the curvable section that is implemented by a driving amount of a corresponding one of actuators (driving units) derived from the data in accordance with the mechanism of the continuum robot when data of the target position of the curvable section is provided.

Modification of the kinematic model is performed by experimentally measuring a curvature of a continuum robot, and obtaining a coefficient (a modification value) for modifying the kinematic model by an algorithm which uses an iterative optimization technique. A kinematic modification matrix can be obtained from the kinematic modification coefficient, and an error between a target shape and a curvature actually implemented by a control system of the continuum robot can be reduced by using an inverse matrix of the kinematic modification matrix.

FIG. 5 is a block diagram of an optimization algorithm for obtaining a kinematic modification coefficient vector $\gamma$ used in the present embodiment. P denotes a continuum robot, and K denotes a block for obtaining an amount of driven displacement of the wire with an angle of a distal end of each curvable section as a target value. First, a first representative shape vector $\theta_{rep[1]}$ which is a predetermined representative position is set, and the driven displacement of the wire $l_{p[1]}$ is obtained by a wire displacement operation block K. Next, the robot P is controlled by applying the driven displacement of the wire, and measurement displacements $X_{ex[9]}$ and $Z_{ex[9]}$ of the curvature of the controlled robot are obtained by using a displacement measurement system of distal ends of the curvable sections illustrated in FIG. 7. A modification coefficient vector $\gamma_{[9]1}$ with respect to the first representative shape is obtained by a steepest descent method operation block SDM by using these measurement displacements, the representative shape vector $\theta_{rep[1]}$, and an initial vector $\gamma_0$ of the modification coefficient. Next, a modification coefficient $\gamma_{[2]1}$ with respect to a second representative shape is obtained in the same manner. In the present embodiment, the modification coefficient $\gamma_{[1]1}$ obtained with respect to the first representative shape is used as an initial value of the steepest descent method with respect to the second representative shape. This avoids setting of the modification coefficient vector to a local minimum value.

Next, a modification coefficient $\gamma_{[a]1}$ is obtained for each of the "a" types of representative shapes ("a" representing a number). The aforementioned procedure is a first trial. Then, a second trial is performed, in which an initial value of a modification coefficient is defined as a modification coefficient $\gamma_{[a]1}$ with respect to each representative shape obtained in the first trial. Thus, the second trial is performed in the same manner as the first trial. Trials are iterated h times and it is determined in the block CJB whether the modification coefficient is sufficiently converged. A mean value of all the modification coefficients is obtained by the mean operation block 1/(ah), and the obtained mean value is defined as a modification coefficient vector $\gamma$. The mean value may be substituted by another value obtained by combining all the modification coefficients. Another value may be a median value, a weighted mean value in consideration of a weight determined depending on a mode of a representative shape, for example. Any combined values which provide sufficient modification effects may be used. The modification coefficient $\gamma_{[a]1}$ and the like can be used as an initial value for modifying the kinematic model in another representative shape (position) by using a modification result in at least one of a plurality of representative shapes (positions).

Hereinafter, derivation of a kinematic model of a continuum robot, a modification coefficient optimization algorithm, and a control system will be described in detail, and control results obtained by experiments will be described.

(1.1 Modeling of Continuum Robot)
(1.1.1 Derivation of Kinematic Model)

FIG. 1 illustrates a schematic diagram of a continuum robot 100 which includes six curvable sections 101 to 106 used in the present embodiment. In the continuum robot 100, driving wires 111 to 116 are connected to distal ends 121 to 126 of the curvable sections 101 to 106, respectively, and positions of the curvable sections 101 to 106 are controlled by pushing and pulling the wires 111 to 116 by actuators 131 to 136, respectively, installed in a robot base 140. In the example illustrated in FIG. 1, the driving wires 111 to 116 are connected to the distal ends 121 to 126 of the curvable sections 101 to 106 alternately on the opposite sides of a central axis, however, positions at which the wires are connected to the curvable sections are not limited thereto. The connecting positions may be arbitrarily determined if the positions of the curvable sections can be controlled by pushing and pulling the wires. The base 140 has a degree of freedom in the z-axis direction and can detect a displacement. FIG. 2 is a schematic diagram of a structure of a first curving section 101 consisting of a housing and the wire 111. In FIGS. 1 and 2, the central axis of the housing is depicted by the broken line or the dash-dot line. The continuum robot further includes a control unit (not illustrated). When a target position is input, the control unit outputs a signal for controlling driving of a corresponding one of the wires by the actuator so that each curvable section obtains the target position. That is, the control unit controls driving of a first wire and a second wire in accordance with a kinematic model which will be described later. The target position may be input by a user or may be input in accordance with a program stored in advance by a target position input unit (not illustrated). Further, the target position may be input as an angle of each curvable section. The control unit may be implemented by one or more processors in a computer loading and executing a program, for example, or may be implemented as a dedicated circuit (FPGA and ASIC).

Definitions of the reference symbols in the following description are as follows. $l_n$: the length of an arm housing in the n-th curvable section; $r_n$: the displacement from the central axis of the arm housing to the wire in the n-th curvable section; e: the number of curvable sections of the robot; $\theta_n$: the angle of the distal end of the n-th curvable section; $\rho_n$: the curvature radius in the n-th curvable section; $\theta_{refn}$: the target angle of the distal end of the n-th curvable section; $l_{pn}$: the driven displacement of the wire in the n-th curvable section; $x_{tn}$, $z_{tn}$: the coordinates of the distal end of the n-th curvable section; c: the evaluation point of the robot; $x_i$, $z_i$: the i-th coordinates when the robot is divided into c in the longitudinal direction; and $z_b$: the displacement of the base.

A kinematic model of a continuum robot with n curvable sections illustrated in FIG. 3 (also see FIG. 4) is derived based on the following assumptions.

1. The housing and the wires deform only horizontal to the drawing plane.
2. In each curvable section, the housing and the wire deform at a constant curvature.
3. Twisting deformation of the housing and the wire is not taken into consideration.
4. The housing and the wire do not deform in the longitudinal direction.
5. A wire guide is provided in the housing, and the center of a circular arc of a central axis of the housing and the center of a circular arc made by the wire coincide with each other all the time.
6. Friction between the housing and the wire is not taken into consideration.

First, a relationship between the driven displacement of the wire and an angle of the distal end of the curvable section is derived. Considering only the first curving section, the relationship between a driving amount $l_{p1}$ of the wire and an angle $\theta_1$ of the distal end of the first curving section is expressed by Expression (1). Here, since Expression (2) holds, Expression (3) is obtained from Expressions (1) and (2). Next, a relationship between the driven displacement of the wire lpn and the angle $\theta_n$ of the distal end of the n-th curvable section is derived. Here, n is 2 or greater. $\tilde{\theta}_n$ ($\theta$ with tilde) which is a curve relative angle in the n-th curvable section is defined by Expression (4). As illustrated in FIG. 3, a relative coordinate system $x_n$-$z_n$ having an origin point ($x_{tn-1}$, $z_{tn-1}$) and having coordinate axes extending in an n-$\theta$1 direction and a direction orthogonal to the n-$\theta$1 direction is established. Then, a relationship between $\tilde{l}_{pn}$ (l with tilde) which is the driven displacement of the wire in the relative coordinate system $x_n$-$z_n$ and $\tilde{\theta}_n$ ($\theta$ with tilde) which is the relative angle of the distal end of the n-th curvable section is expressed by Expression (5). The driven displacement of the wire $l_{pn}$ in the n-th curvable section becomes the sum of the displacements of the wires for driving the n-th curvable section in the relative coordinate system from the first to the (n−1)th sections and is expressed by Expression (6).

$$(\rho_l - r_l)\theta_l + l_{pl} = l_l \quad (1)$$

$$l_l = \rho_l \theta_l \quad (2)$$

$$l_{pl} = r_l \theta_l \quad (3)$$

[Math.1]

$$\tilde{\theta}_n = \theta_n - \theta_{n-1} \quad (4)$$

[Math.2]

$$\tilde{l}_{pn} = r_n \tilde{\theta}_n \quad (5)$$

[Math.3]

$$l_{pn} = r_n(\tilde{\theta}_n + \tilde{\theta}_{n-1} + \ldots + \theta_1) = r_n \theta_n \quad (6)$$

This indicates that the angle $\theta_n$ of the distal end of the n-th curvable section is determined in accordance with only the driven displacement of the wire $l_{pn}$ and not with the angles of the first to the (n-1)th sections.

Next, a relationship between the angle at the distal end of the n-th curvable section and coordinates at the distal end is derived. First, the first curving section will be considered. If $\rho$ is defined as a curvature radius, the coordinates ($x_{t1}$, $z_{t1}$) of the distal end of the first curving section are expressed by Expressions (7) and (8). When Expression (2) is substituted into Expressions (7) and (8), Expressions (9) and (10) are given. Here, a relationship between the angle at the distal end and the coordinates at the distal end of the n-th curvable section is derived. Here, n is 2 or greater. $\tilde{x}_{tn}$ (x with tilde) and $\tilde{z}_{tn}$ (z with tilde) which are coordinates of the distal end of the curvable section in the relative coordinate system $x_c z_n$ are expressed by Expressions (11) and (12).

Therefore, the coordinates ($x_{tn}$, $z_{tn}$) of the distal end in an absolute coordinate system is expressed by Expression (13) by using a rotational transform matrix. In the following section, coordinates for dividing the entire robot into a times are used as evaluation points of an optimization algorithm. The total number of the evaluation points is c=αe and coordinates ($x_i$, $z_i$) of the i-th evaluation point are given by Expression (14). Q is a quotient obtained by Q=[i/α], and R is a remainder obtained by R=i mod α.

$$x_{t1} = \rho_1(1 - \cos\theta_1) \quad (7)$$

$$z_{t1} = \rho_1 \sin\theta_1 \quad (8)$$

[Math. 4]

$$x_{t1} = \frac{l_1}{\theta_1}(1 - \cos\theta_1) \quad (9)$$

[Math. 5]

$$z_{t1} = \frac{l_1}{\theta_1}\sin\theta_1 \quad (10)$$

[Math. 6]

$$\tilde{x}_m = \frac{l_n}{\tilde{\theta}_n}(1 - \cos\tilde{\theta}_n) \quad (11)$$

[Math. 7]

$$\tilde{z}_m = \frac{l_n}{\tilde{\theta}_n}\sin\tilde{\theta}_n \quad (12)$$

[Math. 8]

$$\begin{bmatrix} x_{tn} \\ z_{tn} \end{bmatrix} = \begin{bmatrix} x_{t1} \\ z_b + z_{t1} \end{bmatrix} + \sum_{m=2}^{n} \begin{bmatrix} \cos\theta_{m-1} & \sin\theta_{m-1} \\ -\sin\theta_{m-1} & \cos\theta_{m-1} \end{bmatrix} \begin{bmatrix} \frac{l_m}{\tilde{\theta}_m}(1 - \cos\tilde{\theta}_m) \\ \frac{l_m}{\tilde{\theta}_m}\sin\tilde{\theta}_m \end{bmatrix} \quad (13)$$

-continued

[Math. 9]

$$\begin{bmatrix} x_i \\ z_i \end{bmatrix} = \begin{bmatrix} \frac{l_1}{\left(\frac{R}{\alpha}\right)\theta_1}\left(1 - \cos\left(\frac{R}{\alpha}\right)\theta_1\right) \\ \frac{l_1}{\left(\frac{R}{\alpha}\right)\theta_1}\sin\left(\frac{R}{\alpha}\right)\theta_1 \end{bmatrix} + \begin{bmatrix} 0 \\ z_b \end{bmatrix} (i < \alpha)$$ (14)

$$\begin{bmatrix} x_i \\ z_i \end{bmatrix} = \sum_{n=1}^{Q}\begin{bmatrix} x_{tn} \\ z_{tn} \end{bmatrix} (i = n\alpha)$$

$$\begin{bmatrix} x_i \\ z_i \end{bmatrix} = \sum_{n=1}^{Q}\begin{bmatrix} x_{tn} \\ z_{tn} \end{bmatrix} + \begin{bmatrix} \cos\theta_Q & \sin\theta_Q \\ -\sin\theta_Q & \cos\theta_Q \end{bmatrix}$$

$$\begin{bmatrix} \frac{l_{Q+1}}{\left(\frac{R}{\alpha}\right)\tilde{\theta}_{Q+1}}\left(1 - \cos\left(\frac{R}{\alpha}\right)\tilde{\theta}_{Q+1}\right) \\ \frac{l_{Q+1}}{\left(\frac{R}{\alpha}\right)\tilde{\theta}_{Q+1}}\sin\left(\frac{R}{\alpha}\right)\tilde{\theta}_{Q+1} \end{bmatrix} + \begin{bmatrix} 0 \\ z_b \end{bmatrix}$$

$(i = n\alpha + 1, \ldots, n\alpha + \alpha - 1)$ (1.1.2 Kinematic Model Modification by Adjacent Sections Continuity Models)

In the preceding section, a kinematic model is derived based on the assumptions of 1 to 5, however, the housing and the wire of a robot which is flexible in the curving direction and highly rigid in the longitudinal direction are difficult in a structural design, and thus assumptions 3 and 4 are hardly satisfied actually. Therefore, the relational expression (6) of the curving angle with respect to the driven displacement of the wire does not hold, and an error will be produced between the actual curving angle after control and the target angle. This influence may cause an error in the curving angle not only in the curvable section in which the wire is driven, but also in other sections, and may produce a continuity issue. Then, in the present embodiment, the following assumptions related to the continuity of the curvable sections are added and the kinematic error is modified.

When driving the n-th curvable section to the curving angle θn (θ with tilde), the following continuity occurs. That is, the curving angles in the (n−1)th curvable section and the (n+1)th curvable section increase by $\gamma_{pn}*(\theta_n)$ (θ with tilde) and $\gamma_{dn}*(\theta_n)$ (θ with tilde), respectively, and the curving angle in the n-th curvable section reduces by $(\gamma_{pn}+\gamma_{dn})*(\theta_n)$ (θ with tilde). Here, $\gamma_{pn}$ and $\gamma_{dn}$ are modification coefficients. That is, an angle obtained by multiplying the curve relative angle in the i-th curvable portion by a coefficient γp[i] is added to the curve relative angle in the adjacent (i−1)th curvable portion. Further, an angle obtained by multiplying the curve relative angle in the i-th curvable portion by another coefficient γd[i] is added to the curve relative angle in the adjacent (i+1)th curvable portion, and an angle obtained by multiplying the curve relative angle in the i-th curvable portion by (γp[i]+γd[i]) is subtracted from the curve relative angle in the i-th curvable portion. A modification value is obtained by using such a model (here, i is 2 or greater and equal to or smaller than (the number of curvable portions)−1). The curving angle in the n-th curvable section to be modified based on this assumption is defined as $\theta_{gn}$ (θ with tilde) and is expressed by Expression (15). In the first curving section which is the most proximal end, the curving angle is expressed by Expression (16) and, in the e-th curvable section which is the most distal end, the curving angle is expressed by Expression (17). These Expressions can be expressed as a matrix by Expression (18) which is defined as a modification matrix Γ in the present embodiment. In the modification matrix Γ, i-th row, i-th column is defined as 1−γd[i]−γp[i], i-th row, (i−1)th column is defined as γd[i−1], and i-th row, (i+1)th column is defined as γp[i+1].

A vector γ consisting of a kinematic modification coefficient is defined by Expression (19), and is referred to as a modification coefficient vector. Therefore, coordinates ($x_{gtn}$, $z_{gtn}$) of each of the distal ends of the curvable sections to be modified are expressed by Expression (20). In coordinates ($x_{gi}$, $z_{gi}$) of the i-th evaluation points for dividing the entire robot into α times, θ and θ (θ with tilde) may be substituted by $\theta_g$ and $\theta_g$ (θ with tilde), respectively, in Expression (14). Therefore, description thereof will be omitted.

[Math. 10]

$$\tilde{\theta}_{gn} = \gamma_{dn-1}\tilde{\theta}_{n-1} + \tilde{\theta}_n - (\gamma_{pn} + \gamma_{dn})\tilde{\theta}_n + \gamma_{pn+1}\tilde{\theta}_{n+1}$$ (15)

[Math. 11]

$$\tilde{\theta}_{g1} = \tilde{\theta}_1 - \gamma_{d1}\tilde{\theta}_1 + \gamma_{p2}\tilde{\theta}_2$$ (16)

[Math. 12]

$$\tilde{\theta}_{ge} = \gamma_{de-1}\tilde{\theta}_{e-1} + \tilde{\theta}_e - \gamma_{pe}\tilde{\theta}_e$$ (17)

[Math. 13]

$$\begin{bmatrix} \tilde{\theta}_{g1} \\ \tilde{\theta}_{g2} \\ \vdots \\ \tilde{\theta}_{gn} \\ \vdots \\ \tilde{\theta}_{ge-1} \\ \tilde{\theta}_{ge} \end{bmatrix} = \begin{bmatrix} 1-\gamma_{d1} & \gamma_{p2} & 0 & & \cdots & & 0 \\ \gamma_{d1} & 1-\gamma_{d2}-\gamma_{pe} & \gamma_{p3} & & & & \\ 0 & & \ddots & & \ddots & & \vdots \\ \vdots & & \gamma_{dn-1} & 1-\gamma_{dn}-\gamma_{pn} & \gamma_{pn+1} & & \vdots \\ & & & \ddots & & \ddots & 0 \\ & & & & \gamma_{de2} & 1-\gamma_{de1}-\gamma_{pe1} & \gamma_{pe} \\ 0 & & \cdots & & 0 & \gamma_{de-1} & 1-\gamma_{pe} \end{bmatrix}\begin{bmatrix} \tilde{\theta}_1 \\ \tilde{\theta}_2 \\ \vdots \\ \tilde{\theta}_n \\ \vdots \\ \tilde{\theta}_{e-1} \\ \tilde{\theta}_e \end{bmatrix} = \Gamma\begin{bmatrix} \tilde{\theta}_1 \\ \tilde{\theta}_2 \\ \vdots \\ \tilde{\theta}_n \\ \vdots \\ \tilde{\theta}_{e-1} \\ \tilde{\theta}_e \end{bmatrix}$$ (18)

[Math. 14]

$$\gamma = [\gamma_{p2} \cdots \gamma_{pe} \gamma_{d1} \cdots \gamma_{de-1}] \quad (19)$$

[Math. 15]

$$\begin{bmatrix} x_{gtn} \\ z_{gtn} \end{bmatrix} = \begin{bmatrix} x_{gt1} \\ z_b + z_{gt1} \end{bmatrix} + \sum_{m=2}^{n} \begin{bmatrix} \cos\theta_{gm-1} & \sin\theta_{gm-1} \\ -\sin\theta_{gm-1} & \cos\theta_{gm-1} \end{bmatrix} \begin{bmatrix} \dfrac{l_m}{\tilde{\theta}_{gm}}(1-\cos\tilde{\theta}_{gm}) \\ \dfrac{l_m}{\tilde{\theta}_{gm}}\sin\tilde{\theta}_{gm} \end{bmatrix} \quad (20)$$

(1.1.3 Optimization of Modification Coefficient)

It is difficult to analytically obtain the kinematic modification coefficient described in the preceding section. This is because continuity of the curving angles is caused due to deformation of the housing and the wires by compression force and tension force in the longitudinal direction, and the compression force and tension force varies due to different numbers of the wires passing through each of the curvable sections, or rigidity of the housing nonlinearly varies depending on the curving angles. Further, the assumptions 1, 2, 5, and 6 are not completely satisfied, and which may cause of an error of the curving angle. Then, in the present embodiment, the curvature is experimentally measured and the modification coefficient γ is obtained from a difference between a measurement value and a value of the kinematic model by using the steepest descent method which is an approach of optimization. Since it is not able to select suitable one curvature for optimization of the modification coefficient γ, optimization is performed by iterating h times (h is a plural number) by using a types (a is a plural number) of representative shapes in the present embodiment. This approach is referred to as an extended steepest descent method.

An algorithm of the extended steepest descent method is illustrated in FIG. 5 as a block diagram. The reference symbols in the block diagram are defined as follows: $_{[k]}$ denotes a k-th (less than or equal to a) representative shape, and; denotes a j-th (less than or equal to h) iterative trial.

A k-th representative shape vector $\theta_{rep[k]}$ is expressed by Expression (21), driven displacement of the wire $l_{p[k]}$ with respect to the k-th representative shape is expressed by Expression (22), and measurement displacements $X_{ex[k]}$ and $Z_{ex[k]}$ of the robot is expressed by Expressions (23) and (24), respectively. SDM denotes a steepest descent method algorithm and is a block for obtaining a modification coefficient vector $\gamma_{[k]j}$ which minimizes an evaluation function expressed by Expression (25) through optimization. The modification coefficient vector $\gamma_{[k]j}$ is a modification coefficient vector of the iteration number j with respect to the k-th representative shape.

As described above, in order to obtain the modification coefficient vector γ by the extended steepest descent method by using these blocks, first, the first representative shape vector $\theta_{rep[1]}$ is set and the driven displacement of the wire $l_{p[1]}$ is obtained by the wire displacement block K which operates Expression (6). Next, the robot P is controlled by applying the driven displacement of the wire, and measurement displacements $X_{ex[1]}$ and $Z_{ex[1]}$ of the curvature of the controlled robot are obtained. The modification coefficient vector $\gamma_{[1]1}$ with respect to the first representative shape is obtained by the steepest descent method operation block SDM by using these measurement displacements, the representative shape $\theta_{rep[1]}$, and the initial vector $\gamma_0$ of the modification coefficient. Next, a modification coefficient $\gamma_{[2]1}$ with respect to a second representative shape is obtained in the same manner. In the present embodiment, the modification coefficient $\gamma_{[1]1}$ obtained with respect to the first representative shape is used as an initial value of the steepest descent method with respect to the second representative shape. This avoids setting of the modification coefficient vector to a local minimum value. Then, as illustrated in FIG. 5, a modification coefficient $\gamma_{[k]1}$ is obtained for each of the a types of representative shapes. The aforementioned procedure is a first iterative trial. Next, a second iterative trial is performed, in which an initial value of a modification coefficient is defined as the modification coefficient obtained in the first iterative trial. Thus, the second trial is performed in the same manner as the first trial. The trial is iterated h times and it is determined in a block CJB whether the modification coefficient is sufficiently converged. Alternatively, the iteration number may be determined in advance by trial and error. A mean value of all the modification coefficient vectors is obtained by Expression (26) and the obtained mean value is defined as a modification coefficient γ.

[Math. 16]

$$\theta_{rep[k]} = [\theta_{rep1[k]} \theta_{rep2[k]} \cdots \theta_{repe[k]}]^T \quad (21)$$

[Math. 17]

$$l_{p[k]} = [l_{p1[k]} l_{p2[k]} \cdots l_{pe[k]}]^T \quad (22)$$

[Math. 18]

$$x_{ex[k]} = [x_{ex1[k]} x_{ex2[k]} \cdots x_{exc[k]}]^T \quad (23)$$

[Math. 19]

$$z_{ex[k]} = [z_{ex1[k]} z_{ex2[k]} \cdots z_{exc[k]}]^T \quad (24)$$

[Math. 20]

$$\sum_{i=1}^{c} \sqrt{(x_{exi[k]} - x_{gi})^2 + (z_{exi[k]} - z_{gi})^2} \quad (25)$$

[Math. 21]

$$\gamma = \frac{1}{ah}\sum_{j=1}^{h}\sum_{k=1}^{a} \gamma[k]j \quad (26)$$

(1.2 Control System Design)

The kinematic modification coefficient is applicable not only to modification of a kinematic model of a robot, and calculation of a curvature thereof, but also to control the curvature. A target curvature vector $\theta_{ref}$ consisting of a target angle $\theta_{refn}$ with respect to the n-th curvable section is defined by Expression (27), and a modification curvature vector $\theta_{mod}$ consisting of a modification target angle $\theta_{mod\ n}$ with respect to the n-th curvable section is defined by Expression (28).

In order to control the robot into the target curvature, the modification curvature vector is obtained as expressed by Expression (29) by using the inverse matrix of the modification matrix F. The modification target angle is converted into an absolute coordinate system, and is substituted into the angle θ of Expression (6) to obtain the driven displacement of the wire. In the control system of the present embodiment, the kinematic modification is applicable to control not only the previously set curvature, but also the curvature by real-time operation by adding an additional target vector $\theta_{com}$ of the curvature to the target curvature vector. A block diagram of this control system is illustrated in FIG. 6.

[Math.22]

$$\theta_{ref} = [\theta_{ref1} \theta_{ref2} \ldots \theta_{refe}]^T \quad (27)$$

[Math.23]

$$\theta_{mod} = [\theta_{mod\ 1} \theta_{mod\ 2} \ldots \theta_{mod\ e}]^T \quad (28)$$

[Math.24]

$$\tilde{\theta}_{mod} = \Gamma^{-1} \tilde{\theta}_{ref} \quad (29)$$

(1.3 Experiment)

In this section, effectiveness of modification of the kinematic model using the modification coefficient γ of the kinematic model illustrated with the 2nd and the 3rd Sections, and the curvature control will be described. Parameters of the robot used in the experiment are the lengths of the arm housing $l_1$ to $l_6$=0.010 m, and the number of curvable sections of the robot e=6. The displacement from the central axis of the arm housing to the wire in the n-th curvable section is $r_1=r_3=1.32*10^{-3}$ m, $r_2=r_4=-1.32*10^{-3}$ m, $r_5=1.4*10^{-3}$ m, and $r_6=-1.4*10^{-3}$ m. In the experiment, as illustrated in FIG. 7, markers 201 to 206 are provided at the distal ends in the curvable sections of the continuum robot 100, and displacement of the distal ends in each of the curvable sections (expressed by Expression (30)) is obtained by an image pickup device 210. In the extended steepest descent method, the evaluation point c is defined as c=60. Therefore, the evaluation points other than the distal ends in the curvable sections are obtained by interpolation based on the assumption that the curvable sections have a constant curvature. As representative curved positions, k=2 types of positions, i.e., a shape in which all the curvable sections uniformly curve and a shape having two curved points as expressed by Expressions (31) and (32), are selected.

In the extended steepest descent method algorithm, the iteration number h is defined as h=10, and the modification coefficient γ is a positive number. Therefore, if an element becomes negative, the value is set to 0.1 and optimization is continued. In addition to the representative curvature, a shape $\theta_{cit}$ expressed by Expression (33) for evaluating modification of the kinematic model and controlling performance is prepared.

FIGS. 8A to 8J illustrate responses of optimization of each element of the modification coefficient γ with respect to the number of iterative trial times by the extended steepest descent method algorithm described in Section (1.1.3). FIGS. 8A to 8E illustrate modification coefficients $\gamma_{p2}$ to $_{p6}$, respectively, and FIGS. 8F to 8J illustrate modification coefficients $\gamma_{d1}$ to $_{d5}$, respectively. It is indicated that the modification coefficients $\gamma p_3$, $\gamma p_5$, $\Gamma d_2$, and $\gamma d_4$ are converged in iteration of about 5 times. $\gamma p_4$ and $\gamma d_3$ are vibratory, however, exhibit a tendency of convergence. The rest of the modification coefficients are vibratory, however, it is indicated that more than half of the modification coefficients avoid the local minimum value by the approach of the present embodiment. The modification coefficient vector obtained by substituting into Expression (26) is Expression (34).

[Math. 25]

$$x_{ed} = [x_{ed1} \ldots x_{ed6}]^T, z_{ed} = [z_{ed1} \ldots z_{ed6}]^T \quad (30)$$

[Math. 26]

$$\theta_{rep[1]} = \left[\frac{\pi}{6} \frac{\pi}{6} \frac{\pi}{6} \frac{\pi}{6} \frac{\pi}{6} \frac{\pi}{6}\right]^T \quad (31)$$

[Math. 27]

$$\theta_{rep[2]} = \left[\frac{\pi}{3} \frac{2\pi}{3} \frac{\pi}{3} 0 \frac{\pi}{3} \frac{2\pi}{3}\right]^T \quad (32)$$

$$\theta_{cit} = [-0.3844\ 0.2476\ 0.9044\ 1.0472\ 0.6657\ 0.2718]^T \quad (33)$$

$$\gamma = [0.1048\ 0.0649\ 0.1346\ 0.0600 \quad (34)$$
$$0.0465\ 0.0349\ 0.0150\ 0.0159\ 0.1088\ 0.1511]$$

FIGS. 9A to 9C illustrate curved position responses by modification of a kinematic model using Expression (34). FIGS. 9A and 9B illustrate responses of the representative shapes expressed by Expressions (31) and (32), respectively, and FIG. 9C illustrates a response of the shape for evaluation expressed by Expression (33). The response by the modified kinematic model is depicted by the solid line, the displacement of the distal end of the curvable section measured by the experiment is depicted by the asterisk, and the response of the kinematic model before modification is depicted by the broken line for the comparison. As illustrated in FIGS. 9A and 9B, it is indicated that although a difference is caused between the experimental response and the response of unmodified kinetic model derived based on the assumptions 1 to 6 of Section (1.1.1), the difference with respect to the experimental response can be reduced by modifying the kinematic model which optimizes the modification coefficient γ by using the experimental response. Further, as illustrated in FIG. 9C, it is indicated that since the kinematic model can be modified at substantially the same precision as that of the representative shape also in the curvature for evaluation which is not used for the optimization of the modification coefficient γ, the extended steepest descent method which performs a plurality of iterative operations by using a plurality of representative shapes is effective.

Next, a response by a control system using a modification matrix Γ described in Section (1.2) (hereinafter, referred to as "proposed control system") will be described. FIGS. 10A and 10B illustrate a response of which target curvature is a first representative shape expressed by Expression (31) and, FIGS. 11A and 11B illustrate a response of which target curvature is a shape for evaluation expressed by Expression (33). In FIGS. 10A and 11A, the response at the distal end of the curvable section by the proposed control system is depicted by the round mark, the response by the control system which does not use the modification matrix F (hereinafter, referred to as "conventional control system") is depicted by the asterisk for the comparison, and the target curvature is depicted by the broken line. Further, points are depicted at distal ends in the curvable sections of the target curvature (hereinafter, referred to as "target coordinates at the distal end). Further, regarding the difference between the target curvature at each of the distal ends in each curvable section and the displacement of the control response in FIGS. 10B and 11B, the difference in the response by the proposed control system is depicted by the solid line and the difference in the response by the conventional control system is depicted by the broken line. It is indicated that the proposed control system reduces the difference between the target curvature and the curvature by modifying the control amount of the driven displacement of the wire by using the inverse matrix of the modification matrix F. In the representative shape and the shape for evaluation, there is no large difference in performance for reducing the difference. This indicates that the optimization technique of the modification coefficient using a plurality of representative shapes is effective.

According to the present embodiment, the kinematic model is modified by presenting the model in consideration of continuity of adjacent curvable sections (curvable portions) in addition to the kinematic model of the continuum robot. The model relates to derivation of a modification value (a modification coefficient, a modification coefficient vector, and a modification matrix) for modifying a kinematic model. In order to obtain the modification value, first, the continuum robot is made to obtain a representative shape in accordance with an unmodified kinematic model, and an actual displacement at an arbitrary position (for example, the distal end) in that curvable section is measured. Then, an optimization algorithm using the model for eliminating a difference between the target value and the measurement value is used. Further, a difference between the target position and the actual position in the curvable section of the continuum robot is reduced by modifying the driving amount of the actuator obtained when the data of the target position in the curvable section is provided by using an inverse, such as an inverse matrix, of the modification value of this kinematic model. The continuum robot can be driven and controlled further as intended by using the modification value.

Second Embodiment

In a second embodiment, the present disclosure is applied to follow-the-leader control. The follow-the-leader control is, as illustrated in FIG. 12, controlling subsequent curvable sections to pass the same trajectory as the trajectory along which the curvable section of the most distal end passes. This enable the continuum robot to move forward in a narrow space without being stuck.

(2.1 Optimization of Target Angle of Follow-the-Leader Control)

It is not necessary in the follow-the-leader control that the trajectory is defined in advance, however, the curving angle of the most distal end may be continuously propagated to a subsequent curvable section with a time difference. However, if the entire trajectory is defined in advance as depicted by the broken lines in FIG. 12, control can be performed by optimizing the curvature depending on the displacement in the z direction of the base. This can reduce a trajectory error in the continuum robot as compared with the follow-the-leader control in which the curving angle is propagated. The procedure will be described below.

In the present embodiment, as illustrated by the dash-dot line in FIG. 13, an example in which the trajectory is the same as the total length of the robot will be described. First, as illustrated by the broken line in FIG. 13, a tangent is added to a proximal end of the trajectory and an origin point of the coordinate system is established at the termination thereof. The length of the tangent may be set to the same as that of the total length of the robot. In the present embodiment, the added tangent and the trajectory are referred to as an entire trajectory. Next, the entire trajectory is divided into 2c equal parts by constant velocity spline interpolation, for example, and trajectory evaluation points $P_1$ to $(x_{tr1}, z_{tr1})$ to $P_{2c}$ $(x_{tr2c}, z_{tr2c})$ are set at the divided nodes. The continuum robot is divided into c equal parts in the longitudinal direction as in the first embodiment, and the divided points are defined as evaluation points. In the follow-the-leader control, the displacement of the base is started from $z_b=z_{tr1}=0$ m, and is completed at $z_b=z_{trc}=$nlm (here, n is an integer of e or smaller, and l is the length of the curvable sections which are assumed to be the same in length).

Then, in order to obtain the curvature of the continuum robot which conforms the entire trajectory as the base position moves forward, the following procedure is taken. The c trajectory evaluation points are extracted from the entire trajectory with a trajectory evaluation point $P_\zeta$ ($1<\zeta$ less than or equal to c) as a start point, and the sum of the distances between the c trajectory evaluation points and the c evaluation points of the continuum robot is defined as an evaluation function (expressed by Expression (35)). Then, the curving angle target value vector which minimizes the evaluation function is obtained by the steepest descent method. If a curve target angle when the base is at the $\zeta$-th trajectory evaluation point $P_\zeta$ is defined as $\theta_{ref\zeta}$, a curve target angle matrix $\Theta_{ref}$ (which is expressed by Expression (36)) of e-th row, c-th column may be obtained for the follow-the-leader control in the procedure described above.

Since the number of the curvable sections is limited, the evaluation function of Expression (35) does not necessarily become 0 in some trajectories. Then, a difference between the shape of the curving angle target value obtained by optimization and the shape of the entire trajectory is defined as a mechanical error in the present embodiment, and a difference between the curving angle target value and the curving angle controlled by the wire driving is defined as a control error.

If the entire trajectory is shorter than the robot, the curving angle target value can be generated by using the above-described algorithm by (1) extending the tangent to be added to the most proximal end, or (2) adding the tangent to the distal end. In (1), the length of the tangent to be added to the most proximal end of the trajectory may be set to (the total length of the robot+the total length of the robot—the length of the trajectory). In (2), the tangent may be added to the distal end of the trajectory and set the length to (the total length—length of the trajectory of the robot). In (2), the follow-the-leader control needs to be completed at the coordinates at which the displacement of the base becomes equal to the length of the trajectory.

(2.2 Modification of Kinematic Model)

Although various trajectories may be taken in the follow-the-leader control, the target curvature changes as the base position moves forward also with respect to a single trajectory. It is difficult to select one appropriate curvature as the representative shape, and selecting all the shapes as the representative shapes takes very long time for optimization. Then, also in the follow-the-leader control, the kinematic modification coefficient γ is optimized by the extended steepest descent method using a types of representative shapes as in the first embodiment.

(2.3 Control System Design)

In the follow-the-leader control, the target curvature vector $\theta_{ref\zeta}$ may be extracted from the curve target angle matrix $\Theta_{ref}$ obtained as described in Section (2.1) depending on the displacement of the base $z_b$, the modification curvature vector may be obtained by using an inverse matrix of the modification matrix $\Gamma$ as in the first embodiment, and the driven displacement of the wire may be obtained. In the follow-the-leader control, the kinematic modification is applicable also to the control of the curvature in real-time operation by adding an additional target vector $\theta_{com}$ of the curvature to the target curvature vector. A block diagram of the control system is illustrated in FIG. 14.

(2.4 Experiment)

(2.4.1 Evaluation of Kinematic Modification)

Effectiveness of the kinematic modification algorithm by the extended steepest descent method with respect to the follow-the-leader control will be verified. A C-shape trajectory depicted by the broken line in FIG. 15A and an S-shape trajectory depicted by the broken line in FIG. 15B are used. The number of curvable sections is defined as e=6, and all the curvatures obtained by optimization using Expression (35) with respect to the displacement of the base are superimposed as gray lines. It is indicated that a deviation between the gray area and the broken line becomes a mechanical difference, and the greatest mechanical difference appears near the coordinates (0, nl) which is an entrance of the trajectory. The representative shapes used by the extended steepest descent method are the two shapes expressed by Expressions (31) and (32) as in the first embodiment. Therefore, the modification coefficient vector γ is the same as that of the first embodiment.

A difference response between the curvature by the experiment and the curvature by the kinematic model in the follow-the-leader control with respect to the trajectories of FIGS. 15A and 15B are illustrated in FIGS. 16A and 16B, respectively. Since modification of the kinematic model is verified in this section, driven displacement of the wire compensation of Section (2.3) is not applied. In the present embodiment, the kinematic difference between the curvatures by the experiment and the shapes by the kinematic model in the displacement of the base $z_b$ is defined as the sum of the differences of the displacement of the distal ends of the curvable sections expressed by Expression (37).

[Math. 28]

$$\sum_{i=1}^{c} \sqrt{(x_{tr(\zeta+i)} - x_i)^2 + (z_{tr(\zeta+i)} - z_i)^2} \quad (35)$$

[Math. 29]

$$\Theta_{ref} = [\theta_{ref1} \ \cdots \ \theta_{ref\zeta} \ \cdots \ \theta_{refc}] = \begin{bmatrix} \theta_{ref11} & \cdots & \theta_{ref1c} \\ \vdots & \ddots & \vdots \\ \theta_{refe1} & \cdots & \theta_{refec} \end{bmatrix} \quad (36)$$

[Math. 30]

$$E_{ki}(z_b) = \sum_{n=1}^{6} \sqrt{(x_{gtn} - x_{edn})^2 + (z_{gtn} - z_{edn})^2} \quad (37)$$

A difference by the kinematic model using a modification matrix $\Gamma_{CS}$ obtained by the extended steepest descent method is depicted by the solid line, and an error by an unmodified kinematic model for the comparison is depicted by the dotted line. Further, in the present embodiment, in order to indicate effectiveness of optimization of the modification coefficient vector by iteration, the kinematic error by the modification matrix $\Gamma_C$ obtained only by using the representative shape of Expression (31) without performing iteration is depicted by the broken line. The kinematic error by the modification matrix $\Gamma_S$ obtained by using two types of representative shapes, which are expressed by Expressions (31) and (32) without performing iteration is depicted by the dash-dot line. Both of FIGS. 16A and 16B illustrate that the response by the modification matrix $\Gamma_{CS}$ reduces the kinematic error in all of the sections of the follow-the-leader control as compared with the response by the unmodified kinematic model. Further, the kinematic error is the most reduced in the section when the displacement of the base is $z_b$=0.045 m to 0.06 m where the entire robot enters the trajectory and all the sections are curved. However, the response by the modification matrix $\Gamma_C$ has a greater error as compared with the unmodified kinematic model when the displacement of the base $z_b$=0 m to 0.022 m. Further, the response by the modification matrix $\Gamma_S$ has a greater error as compared with the unmodified kinematic model when the displacement of the base $z_b$=0 m to 0.013 m. This indicates that the modification coefficient optimization algorithm by the extended steepest descent method in the present embodiment is effective to the kinematic modification accompanied by the follow-the-leader control.

(2.4.2 Follow-the-Leader Control Response)

Next, a response by the follow-the-leader control system using the modification matrix $\Gamma$ described in Section (2.3) (hereinafter, referred to as "proposed follow-the-leader control system") will be described. Trajectories are the C-shape trajectory depicted by the broken line in FIG. 15A and the S-shape trajectory depicted by the broken line in FIG. 15B as those in the section above. The solid line and the broken line of FIG. 17 are as follows. The solid line depicts a corresponding one of correction target angles $\theta_{mod1}$ to $\theta_{mod6}$ of each curvable section corresponding to the displacement of the base $z_b$ calculated by the proposed follow-the-leader control system with respect to the trajectory of FIG. 15A. The broken line depicts a corresponding one of target angles $\theta_{ref1}$ to $\theta_{ref6}$ obtained by an unmodified control system (hereinafter, referred to as "conventional follow-the-leader control system"). For example, in the third curvable section, when the fourth curvable section starts curving upon entrance into the trajectory at $z_b$=0.02 m, the third curvable section causes continuity to the curving and curves in the positive direction, so that a trajectory error occurs in the conventional follow-the-leader control system. In order to reduce the trajectory error, it is indicated that the proposed follow-the-leader control system modifies the target angle so that the curving angle of the third curvable section becomes negative in $z_b$=0.03 m to 0.04 m.

FIGS. 18A to 18D illustrate experimental responses of the follow-the-leader control with respect to the C-shape trajectory and FIGS. 19A to 19D illustrate experimental responses of the follow-the-leader control with respect to the S-shape trajectory. FIGS. 18A and 19A each illustrate a difference distance between the coordinates at the distal end and the target coordinates at the distal end of each curvable section with respect to the displacement of the base $z_b$. FIGS. 18B and 19B each illustrate the sum of the distance differences of all the curvable sections. FIGS. 18C and 18D each illustrate a curvature at displacement of the base $z_b$=0.03 m and 0.06 m. The response of the distal end of the curvable section by the proposed follow-the-leader control system is depicted by the round mark, the response of the distal end of the curvable section by the conventional follow-the-leader control system is depicted by the x mark for the comparison, the displacement of the base is depicted by the square mark, and the entire trajectory is depicted by the broken line. The marks in FIGS. 19C and 19D are the same.

The response with respect to the C-shape trajectory illustrated in FIG. 18A indicates that, in the proposed follow-the-leader control system, the distance difference in the sixth curvable section becomes slightly greater near the displacement of the base $z_b$=0.02 m as compared with the conventional follow-the-leader control system. In the sum of the distance differences illustrated in FIG. 18B, the difference is reduced almost to the half with respect to the conventional follow-the-leader control system in the section of the displacement of the base $z_b$=0.02 m to 0.06 m. FIG. 18C indicates that the distance difference by the proposed follow-the-leader control system is small, however, in the conventional follow-the-leader control system, the third and the fourth curvable sections deviate toward the center of curvature of the trajectory. In the shape upon reaching the trajectory termination of FIG. 18D, it is indicated that, in the conventional follow-the-leader control system, the fifth and the sixth curvable sections deviate toward the opposite side of the center of curvature of the trajectory.

The response with respect to the S-shape trajectory illustrated in FIG. 19A indicates that, in the proposed follow-the-leader control system, the distance difference is greater near the displacement of the base $z_b$=0.04 m in the sixth curvable section, and near the displacement of the base $z_b$=0.06 m in the fourth curvable section as compared with the conventional follow-the-leader control system. However, in the sum of the distance differences illustrated in FIG. 19A, the difference is significantly reduced with respect to the conventional follow-the-leader control system in the section of the displacement of the base $z_b$=0.02 m to 0.058 m. FIG. 19C indicates that the distance difference by the proposed follow-the-leader control system is small, however, in the conventional follow-the-leader control system, the third to the fifth curvable sections deviate toward the center of curvature of the trajectory. In the shape upon reaching the trajectory termination of FIG. 18D, it is indicated that, in the conventional follow-the-leader control system, the sixth curvable section deviates toward the opposite side of the center of curvature of the trajectory. Thus, it is indicated that the proposed follow-the-leader control system by the modification matrix $\Gamma_{CS}$ using a plurality of representative shapes has a smaller distance difference from the target angle as compared with the conventional follow-the-leader control system and is able to reduce deviation from the trajectory. Further, since the error reduction performance is not limited to the specific trajectory or the specific section in the trajectory, it is indicated that the proposed follow-the-leader control system is effective to the follow-the-leader control of the continuum robot.

Third Embodiment

In the second embodiment, the trajectory has the curved points whereas the curvature is constant. In the present embodiment, follow-the-leader control is performed to a trajectory of which curvature is not constant. The modification coefficient of the adjacent section continuity model used in the embodiment above is constant with respect to the change of the curving angle, however, in practice, continuity of the curvable section nonlinearly changes in accordance with the curving angle, and the influence of the continuity tends to be saturated relative to an increase in the curving angle. Therefore, in the trajectory with a portion where a curvature is large, modification may become excessive. Then, the present embodiment describes a control system in which an inverse matrix $\Gamma^{-1}$ of a matrix used for the modification of a kinematic model is multiplied by an additional gain $G_{ib}$ as illustrated in FIG. 20.

First, trajectories to be discussed in the present embodiment are illustrated by the broken lines in FIGS. 21A and 21B. As in the second embodiment, the number of curvable sections is defined as e=6, and all the curvatures obtained by optimization using Expression (35) as an evaluation function are superimposed as gray lines. Since the maximum value of the target curving angle of the robot is limited to 60 degrees in the present embodiment, the mechanical error is large in the trajectory illustrated in FIG. 21B. In the present embodiment, the additional gain $G_m$ is obtained by using the trajectory of FIG. 21A. As a procedure, a kinematic modification coefficient is first multiplied by an additional gain, and a curvature of which kinematic model is modified with respect to the displacement of the base of the follow-the-leader control is obtained, then, a kinematic error $E_{ki}(z_b)$ is obtained by an experiment as in the second embodiment. Next, an appropriate additional gain $G_m$ is determined with a mean value and a standard deviation in the entire trajectory of the kinematic error $E_{ki}(z_b)$ as evaluation indices. FIG. 22A illustrates a response of a kinematic error which changes the additional gain $G_m$ from 0 to 1 by 0.1. It is indicated that, in the response of the additional gain $G_m$=0 of an unmodified kinematic model, a kinematic error at a trajectory termination is large. It is indicated that the kinematic error of the trajectory termination reduces as the additional gain $G_m$ approaches 1, whereas the kinematic error increases near the displacement of the base $z_b$=0.04 mm. FIG. 22B illustrates a response in which the additional gain $G_m$ is plotted on the horizontal axis and a mean value and a standard deviation of the kinematic error are plotted on the vertical axis. FIG. 22B illustrates that the mean value of the kinematic error becomes the minimum at the additional gain $G_m$=0.6, and the standard deviation of the kinematic error becomes the minimum at the additional gain $G_m$=0.9. For example, when the image pickup apparatus is installed at the most distal end of the robot, blurring of a captured image can be reduced by reducing the standard deviation of the kinematic error. In consideration of the aforementioned, the additional gain $G_m$ is determined to be 0.7 in the present embodiment.

Next, the response by the follow-the-leader control system using the additional gain (hereinafter, referred to as "modified follow-the-leader control system) will be described. FIGS. 23A, 23B, 23C, and 23D illustrate experimental responses of the follow-the-leader control with respect to the trajectory of FIG. 21A. FIGS. 24A, 24B, 24C, and 24D illustrate experimental responses of the follow-the-leader control with respect to the trajectory of FIG. 21B. The meaning of the axes and the reference symbols of each diagram are the same as those of the second embodiment.

The response illustrated in FIG. 23A indicates that, in the modified follow-the-leader control system, a distance error in the sixth curvable section is slightly larger than that in the conventional follow-the-leader control system at displacement of the base $z_b$=0.02 m to 0.04 m. In the sum of the distance errors illustrated in FIG. 23B, the difference in the modified follow-the-leader control system is reduced in the section of the displacement of the base $z_b$=0.045 m to 0.06 m as compared with the difference in the conventional follow-the-leader control system. FIGS. 23C and 23D illustrate that there is no large difference in performance between the modified follow-the-leader control system and the conventional follow-the-leader control system in the displacement of the base $z_b$=0.03 m, whereas in the shape upon reaching the trajectory termination, the modified follow-the-leader control system has reduced the distance difference in the sixth curvable section.

The responses illustrated in FIGS. 24A and 24B indicate that the modified follow-the-leader control system has significantly reduced the distance difference in all the curvable sections as compared with the conventional follow-the-leader control system. FIGS. 24C and 24D illustrate that there is no large difference in performance between the modified follow-the-leader control system and the conventional follow-the-leader control system in the displacement of the base $z_b$=0.03 m, whereas in the shape upon reaching the trajectory termination, the modified follow-the-leader control system has reduced the distance difference in the fifth and the sixth curvable sections.

Thus, it is indicated that in the follow-the-leader control with respect to the trajectory of constant curvature, a distance difference from the target angle is able to become smaller as compared with the conventional follow-the-leader control system and deviation from the trajectory is able to be reduced by introducing an additional gain. Further, since the difference reduction performance is not limited to the specific trajectory or the specific displacement of the base in the trajectory, it is indicated that the proposed follow-the-leader control system is effective to the follow-the-leader control of the continuum robot.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-138133, filed Jul. 13, 2016, which is hereby incorporated by reference herein in its entirety.

The invention claimed is:

1. A continuum robot, comprising:
    a base;
    a first actuator that is in the base;
    a first wire configured to transmit an actuation force from the first actuator;
    a first curvable portion which is capable of bending in accordance with the actuation force transmitted by the first wire;
    a second actuator that is in the base;
    a second wire configured to transmit an actuation force from the second actuator;
    a second curvable portion provided lengthwise adjacent to the first curvable portion and capable of bending in accordance with the actuation force transmitted by the second wire;
    and
    a controller configured to control the first actuator and the second actuator,
    wherein the controller is comprising:
        a calculator configured to calculate, in accordance with commands corresponding to a target posture of the first curvable portion and a target posture of the second curvable portion, (a) a curve condition of the second curvable portion in accordance with a driving of the first wire and (b) a curve condition of the first curvable portion in accordance with a driving of the second wire;
        a correction portion configured to correct, based on the curve conditions of the first curvable portion and the second curvable portion, the commands; and
        a computation portion configured to compute, based on the corrected commands, driving amounts of the first actuator and the second actuator;
    wherein the controller controls the first actuator and the second actuator based on the driving amounts.

2. The continuum robot, according to claim 1,
wherein the controller controls the driving of the first wire and the driving of the second wire so that the target posture of the first curvable portion is achieved by the sum of curved amounts of the first curvable portion and the second curvable portion.

3. The continuum robot according to claim 1,
wherein the controller performs follow-the-leader control.

4. A control method of a continuum robot,
the continuum robot comprising:
    a base;
    a first actuator that is in the base;
    a first wire configured to transmit an actuation force from the first actuator:
    a first curvable portion which is bent by driving the first wire;
    a second actuator that is in the base;
    a second wire configured to transmit an actuation force from the second actuator:
    a second curvable portion provided lengthwise adjacent to the first curvable portion and is bent by driving the second wire; and
    a controller configured to control the first actuator and the second actuator, and
the method comprising:
    calculating, in accordance with commands corresponding to a target posture of the first curvable portion and a target posture of the second curvable portion, (a) a curve condition of the second curvable portion in accordance with a driving of the first wire and (b) a curve condition of the first curvable portion in accordance with a driving of the second wire;

correcting, based on the curve conditions of the first curvable portion and the second curvable portion, the commands;

computing, based on the corrected commands, driving amounts of the first actuator and the second actuator; and controlling the first actuator and the second actuator based on the driving amounts.

5. The control method of a continuum robot, according to claim 4, further comprising:

using kinematic models of the first and the second curvable potions for controlling driving of the first wire and the second wire so that the target posture of the first curvable portion is achieved by the sum of curved amounts of the first curvable portion and the second curvable portion.

6. The control method of a continuum robot according claim 4, wherein a modification value for modifying a kinematic model of the first curvable portion and a kinematic model of the second curvable portion which represents a relationship between data of a target position of the first curvable portion and a position of the second curvable portion by a driven displacement of the first wire and the second wire respectively derived from the data in accordance with a mechanism of the continuum robot is obtained by an algorithm using an optimization technique to reduce a difference between data of the target position of the first curvable portion when the continuum robot obtains a predetermined position and a measurement value related to an actual position of the first curvable portion.

7. The control method of a continuum robot according to claim 6, wherein a measurement displacement of the second curvable portion controlled by a driven displacement of the second wire in accordance with data of a first predetermined representative position of the continuum robot is obtained, a modification coefficient with respect to the first predetermined representative position is obtained by a steepest descent method by using the measurement displacement, the data of the first predetermined representative position, and an initial value of the modification coefficient, this method is used similarly to a second predetermined representative position to obtain a modification coefficient with respect to the second predetermined representative position, so that the modification coefficient is obtained with respect to each of a plurality of predetermined representative positions, and the modification value is obtained.

8. The control method of a continuum robot according claim 7, wherein the modification coefficient obtained with respect to the first predetermined representative position is used as an initial value of the modification coefficient of the steepest descent method with respect to the second predetermined representative position.

9. The control method of a continuum robot according claim 7, wherein an iterative optimization technique is used, and a modification coefficient obtained in a first previous time is used as an initial value of a modification coefficient of each time.

10. The control method of a continuum robot according claim 7, wherein a mean value of all the modification coefficients is obtained and is defined as the modification value.

11. The control method of a continuum robot according claim 6, wherein the modification value is obtained by using a model in which an angle obtained by multiplying the curve relative angle in the i-th curvable portion by a coefficient $\gamma p[i]$ is added to the curve relative angle in the adjacent (i−1)th curvable portion, an angle obtained by multiplying the curve relative angle in the i-th curvable portion by another coefficient $\gamma d[i]$ is added to the curve relative angle in the adjacent (i+1)th curvable portion, and an angle obtained by multiplying the curve relative angle in the i-th curvable portion by $(\gamma p[i]+\gamma d[i])$ is subtracted from the curve relative angle in the i-th curvable portion (i is 2 or greater and equal to or smaller than (the number of curvable portions)−1).

12. The control method of a continuum robot according claim 11, wherein the modification value is obtained from a modification matrix.

13. The control method of a continuum robot according claim 12, wherein in the modification matrix, i-th row, i-th column is defined as $1-\gamma d[i]-\gamma p[i]$, i-th row, (i−1)th column is defined as $\gamma d[i-1]$, and i-th row, (i+1)th column is defined as $\gamma p[i+1]$.

14. The control method of a continuum robot according to claim 6, further comprising:

obtaining a modified target position by multiplying data of the target position of the first curvable portion by an inverse of a modification value and, controlling the first curvable portion by a driven displacement of the first wire calculated in accordance with the modified target position.

15. The control method of a continuum robot according to claim 14, wherein not only control of a previously set curvature, but also control of a curvature by a real-time operation is performed by adding an additional target value of the curvature to data of the target position of the first curvable portion.

16. The control method of a continuum robot according to claim 14, wherein follow-the-leader control with respect to a trajectory of inconstant curvature is performed by multiplying an inverse of the modification value by an additional gain.

* * * * *